(12) United States Patent
Sharma et al.

(10) Patent No.: US 7,385,025 B2
(45) Date of Patent: *Jun. 10, 2008

(54) METALLOPEPTIDE COMPOUNDS

(75) Inventors: Shubh D. Sharma, Cranbury, NJ (US); Yi-Qun Shi, East Brunswick, NJ (US); Ramesh Rajpurohit, Hillsboro, NJ (US); Hui-Zhi Cai, East Brunswick, NJ (US); Margarita Bastos, Plainsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/188,552

(22) Filed: Jul. 25, 2005

(65) Prior Publication Data

US 2005/0282739 A1  Dec. 22, 2005

Related U.S. Application Data

(63) Continuation-in-part of application No. 10/769,695, filed on Jan. 30, 2004, and a continuation-in-part of application No. 10/464,117, filed on Jun. 17, 2003, which is a continuation-in-part of application No. PCT/US01/50075, filed on Dec. 19, 2001.

(60) Provisional application No. 60/590,933, filed on Jul. 23, 2004, provisional application No. 60/444,129, filed on Jan. 31, 2003, provisional application No. 60/327,835, filed on Oct. 4, 2001, provisional application No. 60/304,835, filed on Jul. 11, 2001, provisional application No. 60/256,842, filed on Dec. 19, 2000.

(51) Int. Cl.
*A61K 38/04* (2006.01)
*A61K 51/08* (2006.01)
*C07K 7/00* (2006.01)

(52) U.S. Cl. ............ 530/300; 530/326; 530/327; 530/328; 530/329; 530/330; 530/331; 435/7.1; 424/1.69

(58) Field of Classification Search ............... 435/7.1; 530/300, 326, 327, 328, 329, 330, 331; 424/1.69
See application file for complete search history.

(56) References Cited

U.S. PATENT DOCUMENTS

| | | | |
|---|---|---|---|
| 4,390,528 A | 6/1983 | Najjar | |
| 4,427,646 A | 1/1984 | Olexa et al. | |
| 4,479,930 A | 10/1984 | Hnatowich | |
| 4,578,079 A | 3/1986 | Ruoslahti et al. | |
| 4,650,787 A | 3/1987 | Schalley et al. | |
| 4,668,503 A | 5/1987 | Hnatowich | |
| 4,680,276 A | 7/1987 | Bach et al. | |
| 4,732,864 A | 3/1988 | Tolman | |
| 4,849,505 A | 7/1989 | Stavrianopoulos | |
| 4,859,765 A | 8/1989 | Nestor, Jr. et al. | |
| 4,863,898 A | 9/1989 | Ashmead et al. | |
| 4,883,861 A | 11/1989 | Grill et al. | |
| 4,986,979 A | 1/1991 | Morgan, Jr. et al. | |
| 5,023,237 A | 6/1991 | Pickart | |
| 5,028,593 A | 7/1991 | Nishioka | |
| 5,059,588 A | 10/1991 | Pickart | |
| 5,091,176 A | 2/1992 | Braatz et al. | |
| 5,118,665 A | 6/1992 | Pickart | |
| 5,157,023 A | 10/1992 | Lipton | |
| 5,196,510 A | 3/1993 | Rodwell et al. | |
| 5,200,504 A | 4/1993 | Ghadiri | |
| 5,214,131 A | 5/1993 | Sano et al. | |
| 5,225,180 A | 7/1993 | Dean et al. | |
| 5,328,840 A | 7/1994 | Coller | |
| 5,371,184 A | 12/1994 | Rajagopalan et al. | |
| 5,382,654 A | 1/1995 | Lyle et al. | |
| 5,395,609 A | 3/1995 | Stuttle | |
| 5,408,036 A | 4/1995 | Ghadiri | |
| 5,410,020 A | 4/1995 | Ghadiri | |
| 5,438,119 A | 8/1995 | Rutter et al. | |
| 5,440,013 A | 8/1995 | Kahn | |
| 5,443,815 A | 8/1995 | Dean et al. | |
| 5,443,816 A | 8/1995 | Zamora et al. | |
| 5,464,934 A | 11/1995 | Dunn et al. | |
| 5,470,753 A | 11/1995 | Sepetov et al. | |

(Continued)

FOREIGN PATENT DOCUMENTS

| | | |
|---|---|---|
| CA | 2016235 | 9/1990 |
| EP | 94810008.6 | 1/1994 |
| WO | PCT/US92/00757 | 2/1992 |
| WO | PCT/US92/10716 | 11/1992 |
| WO | PCT/US93/02320 | 3/1993 |
| WO | PCT/US93/03687 | 4/1993 |

(Continued)

OTHER PUBLICATIONS

Pinilla, C., et al., "A Review of the Utility of Soluble Peptide Combinatorial Libraries", *Biopolymers (Peptide Science)*, vol. 37, (1995) 221-240.

(Continued)

*Primary Examiner*—Chih-Min Kam
(74) *Attorney, Agent, or Firm*—Stephen A. Slusher

(57) ABSTRACT

Metallopeptides with a sequence of a biologically active alpha-melanocyte stimulating hormone (α-MSH), gamma-melanocyte stimulating hormone (γ-MSH), or bombesin sequence of length n residues, wherein a residue including a nitrogen atom and sulfur atom each available for complexation to a metal ion is inserted at any position from between the two and three position to the C-terminus side of the n position, or alternatively is substituted for the residue at any position from the three position to the n position, with a metal ion complexed thereto, with any proline (Pro) residue which is either of the two residues on the immediately adjacent N-terminus side of the inserted or substituent residue comprising a nitrogen atom and sulfur atom available for complexation to a metal ion is substituted with a homolog.

10 Claims, No Drawings

U.S. PATENT DOCUMENTS

| | | | |
|---|---|---|---|
| 5,475,085 A | 12/1995 | Kahn | |
| 5,498,538 A | 3/1996 | Key et al. | |
| 5,556,609 A | 9/1996 | Zamora | |
| 5,565,325 A | 10/1996 | Blake | |
| 5,569,745 A | 10/1996 | Goodbody et al. | |
| 5,668,254 A | 9/1997 | Deghenghi | |
| 5,670,155 A | 9/1997 | Kahn | |
| 5,770,178 A | 6/1998 | Itaya et al. | |
| 6,048,527 A | 4/2000 | Granoff et al. | |
| 7,049,398 B1 * | 5/2006 | Sharma et al. | 530/328 |
| 2001/0009899 A1 | 7/2001 | Keri et al. | |
| 2002/0012948 A1 | 1/2002 | Sharma et al. | |

FOREIGN PATENT DOCUMENTS

| | | |
|---|---|---|
| WO | PCT/US93/04794 | 5/1993 |
| WO | PCT/US93/05372 | 6/1993 |
| WO | PCT/US93/06029 | 6/1993 |
| WO | PCT/US94/06274 | 6/1994 |
| WO | PCT/US94/08335 | 7/1994 |
| WO | WO 97/33626 | 9/1997 |
| WO | WO 99/10016 | 3/1999 |

OTHER PUBLICATIONS

Fattorusso, R., et al., "Design of Metal Ion Binding Peptides", *Biopolymers (Peptide Science)*, vol. 37, (1995) 401-410.

Morgan, E.J., et al., "Novel Biopolymers for Drug Discovery", *Biopolymers (Peptide Science)*, vol. 37, (1995) 213-219.

Lebl, M., et al., "One-Bead-One-Structure Combinatorial Libraries", *Biopolymers (Peptide Science)*, vol. 37, (1995) 177-198.

Still, W.C., "Discovery of Sequence-Selective Peptide Binding by Synthetic Receptors Using Encoded Combinatorial Libraries", *Acc. Chem. Res.*, vol. 29, No. 3, (1996) 155-163.

Gordon, E.M., et al., "Strategy and Tactics in Combinatorial Organic Synthesis, Applications to Drug Discovery", *Acc. Chem. Res.*, vol. 29, No. 3, (1996) 144-154.

Ellman, J.A., "Design Synthesis, and Evaluation of Small-Molecule Libraries", *Acc. Chem. Res.*, vol. 29, No. 3., (1996) 132-143.

Armstrong, R.W., et al., "Multiple-Component Condensation Strategies for Combinatorial Library Synthesis", *Acc. Chem. Res.*, vol. 29, No. 3, (1996) 132-131.

Czarnik, A.W., "Guest Editorial", *Acc. Chem. Res.*, vol. 29, No. 3, (1996) 112-113.

Thompson, L.A., et al., "Synthesis and Applications of Small Molecule Libraries", *Chem Reg.*, vol. 96, No. 1, (1996) 555-600.

Dewit, S.H., et al., "Combinatorial Organic Synthesis Using Parke-Davis's DIVERSOMER Method", *Acc. Chem. Res.*, vol. 29, No. 3, (1996) 114-122.

Holmes, C.P., et al., "The Use of Light-Directed Combinatorial Peptide Synthesis in Epitope Mapping", *Bioploymers (Peptide Science)*, vol. 37, (1995) 199-211.

Berg, J.M., et al., "The Galvanization of Biology: A Growing Appreciation for the Roles of Zinc", *Science*, vol. 271, (Feb. 23, 1996) 1081-1085.

Fischman, A.J., et al., "Imaging Focal Sites of Bacterial Infection in Rats wit Indium-111-Labelled Chemotactic Peptide Analogs", *The Journal of Nuclear Medicine*, vol. 32, No. 3, (Mar. 1991) 483-491.

Janeczel, A.H., et al., "Autoradiographic analysis of formylpeptide chemoattractant binding, uptake and intracellular processing by neutrophils", *Journal of Cell Science 94*, (1989) 155-168.

Babich, J.W., et al., "Technetium-99-m-Labeled Chemotactic peptides: Comparison with Indium-111-Labeled White Blood Cells for Localizing Acute Bacterial Infection in the Rabbit", *Jour. Nuc. Med.*, vol. 34, No. 12, (1993) 2176-2181.

Imura, Y., et al., "Antithrombotic Properties of L-Cystein, N-(mercaptoacetyl)-D-Tyr-Arg-Gly-Asp-Sulfoxide (GA4120) in a Hamster Platelet-Rich Femoral Vein Thrombosis Model", *Blood*, vol. 80, No. 5, (1992) 1247-1263.

Fabris, D., et al., "Investigation of Zinc Chelation in Zinc-Finger Arrays by Electrospray Mass Spectrometry", *Inorganic Chemistry*, vol. 38, (1999), 1322-1325.

Giblin, Michael F., et al., "Design and Characterization of (A)-melanocortin Peptide Analogs Cyclized through Rhenium and Technetium Metal Coordination", *Proceedings of National Academy Science USA*, Vo., 95 (Oct. 1998), 12814-12818.

Shi, Yi-Qun, et al., "Conformationally Constrained Metallpeptide Template for Melanocortin-1 Receptor", *American Chemical Society*, 218th *ACS National Meeting, Abstracts of Papers, Part 1, Abstract MEDI 257.U* (Aug. 22, 1999).

Hruby, V.M., Conformational Restrictions of Biologically Active Peptides Via Amino Acid Side Chain Groups:, *Life Sciences*, vol. 31, 189-199, (1982).

Vanbilloen, H.P., et al., "Complexes of Technetium-99m with Tetrapeptides, a New Class of Tc-labelled Agents", *Nuc. Med. Bio.*, 22, 325-357, (1995).

Ghadiri, M.R., et al., "Secondary Structure Nucleation in Peptides, Transition Metal Ion Stabilized a-Helices", *J. Am. Chem. Soc.*, vol. 112, (1990) 1630-1632.

Ghadiri, M.R., et al., "Peptide Architecture, Design of Stable a Helical Metallopeptides via a Novel Exchange-Inert Ru iii Complex", *J. Am. Chem. Soc.*, vol. 112, (1990) 9633-9635.

Ghadiri, M.R., et al., "A Convergent Approach to Protein Design, Metal Ion-Assisted Spontaneous Self-Assembly of a Polypeptide into a Triple-Helix Bundle Protein", *J. Am. Chem. Soc.*, vol. 114, No. 3, (1992) 825-831.

Singh, P.R., et al., "Synthesis and Radiochemical Studies of Model Chelators for Tc-99m", *Proceedings of the 43rd Annual Meeting, Journal of Nuclear Medicine*, (Jun. 4, 1996) p. 28.

Knight, L.C., et al., "Thrombus Imaging with Technetium-99m Synthetic Peptides Based upon the Binding Domain of a Monoclonal Antibody to Activated Platelets", *Jour. Nuc. Med.*, vol. 35, No. 2, (1994), 282-288.

Swanson, D., et al., "In-111 Laminin peptide Fragments for malignant Tumor Detection", *Jour. Nuc. Med.*, vol. 34, No. 5, (1993) 231P.

Wraignt, E.P., et al., "The use of a chelting derivative of alpha melanocyte stimulating hormone for the clinical imaging of malignant melanoma", *British Journal of Radiology*, vol. 65, (1992) 112-118.

Bard, D.R., et al., "BisMSH-DTPA A Potential Imaging Agent for Malignant Melanoma", *Annals of New York Academy of Sciences*, vol. 680, (1993) 451-453.

Chou, P.Y., "Prediction of The Secondary Structure of Proteins from Their Amino Acid Sequence", *Graduate Department of Biochemistry, Brandeis University, Pub. No. 1195*, p. 45-148, Advances in Enzymology and Related Areas of Molecular Biology (1978) 47 45-148.

Hruby, V.J., et al., "Protein and Amino Acid Chemistry", *Synthetic Peptides, A User's Guide*, (1992) 11-24.

Hom, R.K., et al., "Bis(Aminothiol) Oxorhenium Complexes Whose Structure Mimic Steroids", *J. Nuc. Med.*, (Jun. 14, 1995) 68P.

Hruby, V.J., et al., "Conformational Design and Constraint", *Synthetic Peptides, A User's Guide*, (1992) 58-67.

Hruby, V.J., et al., "Applications of Synthetic Peptides", *Synthetic Peptides, A User's Guide, Chapter 5*, (1992) 259-345.

Vallee, B.L., et al., "Zinc Coordination, Function, and Structure of Zinc Enzymes and Other Proteins", *Biochemistry*, vol. 29, No. 24, 5647-5659, (1990).

Rhodes, D., "Zinc Fingers", *Scientific American*, (Feb. 1993) 56-65.

Krizek, B.A., "A Consensus Zinc Finger peptide: Design, High-Affinity Metal Binding, a pH-Dependent Structure, and a His to Cys Sequence Variant", *H. Am. Chem. Soc.*, vol. 113, No. 12, (1991) 4518-4523.

Shaw, G.S., et al., "Calcium-Induced Peptide Association to Form an Intact Protein Domain: 1H NMR Structure Evidence", *Science*, (Jul. 1990) 280-283.

Reid, R.E., et al., "Calcium-induced protein Folding: Structure-Affinity Relationships in Synthetic Analogs of the Helix-Loop-Helix Calcium Binding Unit", *J. Bio Chem.* vol. 256, No. 6, (1981) 2742-2751.

Lieberman, M., et al., "Iron (II) Organizes a Synthetic Peptide into Three-Helix Bundles", *J. Am. Chem. Soc.*, vol. 113, No. 4, (1991) 1470-1471.

Toniolo, C., "Conformationally restricted peptides through short-range cyclizations", *Int. J. Peptide Protein. Res.* 35, (1990) 287-300.

Schwyzer, R., "Peptide-Membrane Interactions and a New Principle in Quantitative Structure-Activity Relationships", *Biopolymers*, vol. 31, (1991) 785-792.

Ozeki, E., et al., "Conformation and complexation with metal ions of cyclic hexapeptides: cyclo (L-Leu-L-Phe-L-Pro)2 and cyclo [L-Cys(Acm)-L-Phe-L-Pro]2" *Int. J. Peptide Protein, Res. 34*, (1989) 111-117.

"Design, Synthesis, and Complexing Properties of (1-Cys-1'Cys,4-Cys-4'Cys)-dithiobis(Ac-L1Cys-L-Pro-D-Val-L-4Cys-NH2)", The First Example of New Family of Ion-Binding Peptides, *J. Am. Chem. Soc.*, vol. 115-125, 11664-11670.

Chi, D.Y., et al., "Homodimeric and heterodimeric Bis(amino thiol) Oxometal Complexes with Rhenium(V) and Technetium(V), Control of Heterodimeric Complex Formulation and an Approach to metal Complexs that Mimic Steroid Horomones", J. Med Chem., vol. 37, No. 7, (1994) 928-937.

Hruby, V.J., "Protein Structure", *Synthetic Peptides, User's Guide*, (1992), 24-33.

Hruby, V.J., "Secondary Structure Predicition", *Synthetic Peptides, A User's Guide*, 39-41, (1992).

\* cited by examiner

SEQUENCE LISTING

```
<160> NUMBER OF SEQ ID NOS: 72

<210> SEQ ID NO 1
<211> LENGTH: 13
<212> TYPE: PRT
<213> ORGANISM: Artificial
<220> FEATURE:
<223> OTHER INFORMATION: alpha-MSH analog specific for melanocortin
      receptors with Nle substitution for Met
<220> FEATURE:
<221> NAME/KEY: MISC_FEATURE
<222> LOCATION: (4)..(4)
<223> OTHER INFORMATION: Norleucine

<400> SEQUENCE: 1
```

```
Ser Tyr Ser Xaa Glu His Phe Arg Trp Gly Lys Pro Val
1               5                   10

<210> SEQ ID NO 2
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 2

Ser Tyr Ser Xaa Glu His Phe Arg Trp Gly Lys Gly Val Cys
1               5                   10

<210> SEQ ID NO 3
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 3

Ser Tyr Ser Xaa Glu His Phe Arg Trp Gly Lys Gly Cys Val
1               5                   10

<210> SEQ ID NO 4
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: misc_feature
<222> LOCATION: (4)..(4)
<223> OTHER INFORMATION: Norleucine

<400> SEQUENCE: 4

Ser Tyr Ser Xaa Glu His Phe Arg Trp Gly Lys Cys Pro Val
1               5                   10

<210> SEQ ID NO 5
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 5

Ser Tyr Ser Xaa Glu His Phe Arg Trp Gly Cys Lys Pro Val
1               5                   10

<210> SEQ ID NO 6
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
```

```
<221> NAME/KEY: MISC_FEATURE
<222> LOCATION: (4)..(4)
<223> OTHER INFORMATION: Norleucine

<400> SEQUENCE: 6

Ser Tyr Ser Xaa Glu His Phe Arg Trp Cys Gly Lys Pro Val
1               5                   10

<210> SEQ ID NO 7
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 7

Ser Tyr Ser Xaa Glu His Phe Arg Cys Trp Gly Lys Pro Val
1               5                   10

<210> SEQ ID NO 8
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 8

Ser Tyr Ser Xaa Glu His Phe Cys Arg Trp Gly Lys Pro Val
1               5                   10

<210> SEQ ID NO 9
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: misc_feature
<222> LOCATION: (4)..(4)
<223> OTHER INFORMATION: Xaa can be any naturally occurring amino acid

<400> SEQUENCE: 9

Ser Tyr Ser Xaa Glu His Phe Cys Arg Trp Gly Lys Pro Val
1               5                   10

<210> SEQ ID NO 10
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 10

Ser Tyr Ser Xaa Glu Cys His Phe Arg Trp Gly Lys Pro Val
1               5                   10

<210> SEQ ID NO 11
```

```
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (4)..(4)
<223> OTHER INFORMATION: Norleucine

<400> SEQUENCE: 11

Ser Tyr Ser Xaa Cys Glu His Phe Arg Trp Gly Lys Pro Val
1               5                   10

<210> SEQ ID NO 12
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (5)..(5)
<223> OTHER INFORMATION: Norleucine

<400> SEQUENCE: 12

Ser Tyr Ser Cys Xaa Glu His Phe Arg Trp Gly Lys Pro Val
1               5                   10

<210> SEQ ID NO 13
<211> LENGTH: 14
<212> TYPE: PRT
<213> ORGANISM: Artificial
<220> FEATURE:
<223> OTHER INFORMATION: metallopeptide derived from alpha-MSH analog
<220> FEATURE:
<221> NAME/KEY: MISC_FEATURE
<222> LOCATION: (5)..(5)
<223> OTHER INFORMATION: Norleucine

<400> SEQUENCE: 13

Ser Tyr Cys Ser Xaa Glu His Phe Arg Trp Gly Lys Pro Val
1               5                   10

<210> SEQ ID NO 14
<211> LENGTH: 11
<212> TYPE: PRT
<213> ORGANISM: Artificial
<220> FEATURE:
<223> OTHER INFORMATION: Nle-3 substituted gamma-MSH analog for
      melanocortin receptors
<220> FEATURE:
<221> NAME/KEY: MISC_FEATURE
<222> LOCATION: (3)..(3)
<223> OTHER INFORMATION: Norleucine

<400> SEQUENCE: 14

Tyr Val Xaa Gly His Phe Arg Trp Asp Arg Phe
1               5                   10

<210> SEQ ID NO 15
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine
```

-continued

<400> SEQUENCE: 15

Tyr Val Xaa Gly His Phe Arg Trp Asp Arg Phe Cys
1               5                   10

<210> SEQ ID NO 16
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 16

Tyr Val Xaa Gly His Phe Arg Trp Asp Arg Cys Phe
1               5                   10

<210> SEQ ID NO 17
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 17

Tyr Val Xaa Gly His Phe Arg Trp Asp Cys Arg Phe
1               5                   10

<210> SEQ ID NO 18
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 18

Tyr Val Xaa Gly His Phe Arg Trp Cys Asp Arg Phe
1               5                   10

<210> SEQ ID NO 19
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 19

Tyr Val Xaa Gly His Phe Arg Cys Trp Asp Arg Phe
1               5                   10

```
<210> SEQ ID NO 20
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 20

Tyr Val Xaa Gly His Phe Cys Arg Trp Asp Arg Phe
1               5                   10

<210> SEQ ID NO 21
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 21

Tyr Val Xaa Gly His Cys Phe Arg Trp Asp Arg Phe
1               5                   10

<210> SEQ ID NO 22
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 22

Tyr Val Xaa Gly Cys His Phe Arg Trp Asp Arg Phe
1               5                   10

<210> SEQ ID NO 23
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
<220> FEATURE:
<221> NAME/KEY: MISC_FEATURE
<222> LOCATION: (3)..(3)
<223> OTHER INFORMATION: Norleucine

<400> SEQUENCE: 23

Tyr Val Xaa Cys Gly His Phe Arg Trp Asp Arg Phe
1               5                   10

<210> SEQ ID NO 24
<211> LENGTH: 12
<212> TYPE: PRT
<213> ORGANISM: Artificial
<220> FEATURE:
<223> OTHER INFORMATION: metallopeptide derived from Nle-3 substituted
      gamma-MSH analog
```

```
<220> FEATURE:
<221> NAME/KEY: MISC_FEATURE
<222> LOCATION: (4)..(4)
<223> OTHER INFORMATION: Norleucine

<400> SEQUENCE: 24

Tyr Val Cys Xaa Gly His Phe Arg Trp Asp Arg Phe
 1               5                  10

<210> SEQ ID NO 25
<211> LENGTH: 14
<212> TYPE: PRT
<213> ORGANISM: Artificial
<220> FEATURE:
<223> OTHER INFORMATION: Bombesin analog derived from amphibian skin
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 25

Xaa Gln Arg Leu Gly Asn Gln Trp Ala Val Gly His Leu Xaa
 1               5                  10

<210> SEQ ID NO 26
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 26

Xaa Gln Arg Leu Gly Asn Gln Trp Ala Val Gly His Leu Xaa Cys
 1               5                  10                  15

<210> SEQ ID NO 27
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 27

Xaa Gln Arg Leu Gly Asn Gln Trp Ala Val Gly His Leu Cys Xaa
 1               5                  10                  15

<210> SEQ ID NO 28
<211> LENGTH: 15
<212> TYPE: PRT
<213> ORGANISM: Artificial
<220> FEATURE:
```

```
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 28

Xaa Gln Arg Leu Gly Asn Gln Trp Ala Val Gly His Cys Leu Xaa
 1               5                  10                  15

<210> SEQ ID NO 29
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 29

Xaa Gln Arg Leu Gly Asn Gln Trp Ala Val Gly Cys His Leu Xaa
 1               5                  10                  15

<210> SEQ ID NO 30
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 30

Xaa Gln Arg Leu Gly Asn Gln Trp Ala Val Cys Gly His Leu Xaa
 1               5                  10                  15

<210> SEQ ID NO 31
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 31

Xaa Gln Arg Leu Gly Asn Gln Trp Ala Cys Val Gly His Leu Xaa
 1               5                  10                  15
```

<210> SEQ ID NO 32
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 32

Xaa Gln Arg Leu Gly Asn Gln Trp Cys Ala Val Gly His Leu Xaa
1               5                   10                  15

<210> SEQ ID NO 33
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 33

Xaa Gln Arg Leu Gly Asn Gln Cys Trp Ala Val Gly His Leu Xaa
1               5                   10                  15

<210> SEQ ID NO 34
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 34

Xaa Gln Arg Leu Gly Asn Cys Gln Trp Ala Val Gly His Leu Xaa
1               5                   10                  15

<210> SEQ ID NO 35
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 35

-continued

```
Xaa Gln Arg Leu Gly Cys Asn Gln Trp Ala Val Gly His Leu Xaa
1               5                   10                  15
```

<210> SEQ ID NO 36
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 36

```
Xaa Gln Arg Leu Cys Gly Asn Gln Trp Ala Val Gly His Leu Xaa
1               5                   10                  15
```

<210> SEQ ID NO 37
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (15)..(15)
<223> OTHER INFORMATION: Norleucine

<400> SEQUENCE: 37

```
Xaa Gln Arg Cys Leu Gly Asn Gln Trp Ala Val Gly His Leu Xaa
1               5                   10                  15
```

<210> SEQ ID NO 38
<211> LENGTH: 15
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (15)..(15)
<223> OTHER INFORMATION: Norleucine
<220> FEATURE:
<221> NAME/KEY: misc_feature
<222> LOCATION: (15)..(15)
<223> OTHER INFORMATION: Norleucine

<400> SEQUENCE: 38

```
Ala Gln Cys Arg Leu Gly Asn Gln Trp Ala Val Gly His Leu Xaa
1               5                   10                  15
```

<210> SEQ ID NO 39
<211> LENGTH: 5
<212> TYPE: PRT
<213> ORGANISM: Artificial
<220> FEATURE:
<223> OTHER INFORMATION: Metallopeptide core sequence derived from
      bombesin analog

<400> SEQUENCE: 39

Trp Ala Val Cys His

```
<210> SEQ ID NO 40
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid

<400> SEQUENCE: 40

Xaa Gln Arg Leu Gly Asn Gln Trp Ala Val Gly His Leu Cys
1               5                   10

<210> SEQ ID NO 41
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 41

Xaa Gln Arg Leu Gly Asn Gln Trp Ala Val Gly His Cys Xaa
1               5                   10

<210> SEQ ID NO 42
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 42

Xaa Gln Arg Leu Gly Asn Gln Trp Ala Val Gly Cys Leu Xaa
1               5                   10

<210> SEQ ID NO 43
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 43
```

Xaa Gln Arg Leu Gly Asn Gln Trp Ala Val Cys His Leu Xaa
1               5                   10

<210> SEQ ID NO 44
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 44

Xaa Gln Arg Leu Gly Asn Gln Trp Ala Cys Gly His Leu Xaa
1               5                   10

<210> SEQ ID NO 45
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 45

Xaa Gln Arg Leu Gly Asn Gln Trp Cys Val Gly His Leu Xaa
1               5                   10

<210> SEQ ID NO 46
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 46

Xaa Gln Arg Leu Gly Asn Gln Cys Ala Val Gly His Leu Xaa
1               5                   10

<210> SEQ ID NO 47
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 47

Xaa Gln Arg Leu Gly Asn Cys Trp Ala Val Gly His Leu Xaa
1               5                   10

<210> SEQ ID NO 48
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 48

Xaa Gln Arg Leu Gly Cys Gln Trp Ala Val Gly His Leu Xaa
1               5                   10

<210> SEQ ID NO 49
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 49

Xaa Gln Arg Leu Cys Asn Gln Trp Ala Val Gly His Leu Xaa
1               5                   10

<210> SEQ ID NO 50
<211> LENGTH: 14
<212> TYPE: PRT
<213> ORGANISM: Artificial
<220> FEATURE:
<223> OTHER INFORMATION: metallopeptide derived from bombesin analog
<220> FEATURE:
<221> NAME/KEY: MISC_FEATURE
<222> LOCATION: (1)..(1)
<223> OTHER INFORMATION: Pyroglutamic acid
<220> FEATURE:
<221> NAME/KEY: MISC_FEATURE
<222> LOCATION: (14)..(14)
<223> OTHER INFORMATION: Norleucine

<400> SEQUENCE: 50

Xaa Gln Arg Cys Gly Asn Gln Trp Ala Val Gly His Leu Xaa
1               5                   10

<210> SEQ ID NO 51
<211> LENGTH: 14
<212> TYPE: PRT
<213> ORGANISM: Artificial
<220> FEATURE:
<223> OTHER INFORMATION: metallopeptide derived from bombesin analog
<220> FEATURE:

```
<221> NAME/KEY: MISC_FEATURE
<222> LOCATION: (14)..(14)
<223> OTHER INFORMATION: Norleucine

<400> SEQUENCE: 51

Ala Gln Cys Leu Gly Asn Gln Trp Ala Val Gly His Leu Xaa
1               5                   10

<210> SEQ ID NO 52
<211> LENGTH: 8
<212> TYPE: PRT
<213> ORGANISM: Artificial
<220> FEATURE:
<223> OTHER INFORMATION: metallopeptide derived from bombesin analog

<400> SEQUENCE: 52

Gln Trp Ala Val Cys His Leu Leu
1               5

<210> SEQ ID NO 53
<211> LENGTH: 7
<212> TYPE: PRT
<213> ORGANISM: Artificial
<220> FEATURE:
<223> OTHER INFORMATION: metallopeptide derived from bombesin analog

<400> SEQUENCE: 53

Trp Ala Val Cys His Leu Leu
1               5

<210> SEQ ID NO 54
<211> LENGTH: 6
<212> TYPE: PRT
<213> ORGANISM: Artificial
<220> FEATURE:
<223> OTHER INFORMATION: metallopeptide derived from bombesin analog

<400> SEQUENCE: 54

Ala Val Cys His Leu Leu
1               5

<210> SEQ ID NO 55
<211> LENGTH: 7
<212> TYPE: PRT
<213> ORGANISM: Artificial
<220> FEATURE:
<223> OTHER INFORMATION: metallopeptide derived from bombesin analog

<400> SEQUENCE: 55

Gln Trp Ala Val Cys His Leu
1               5

<210> SEQ ID NO 56
<211> LENGTH: 6
<212> TYPE: PRT
<213> ORGANISM: Artificial
<220> FEATURE:
<223> OTHER INFORMATION: metallopeptide derived from bombesin analog

<400> SEQUENCE: 56

Trp Ala Val Cys His Leu
1               5

<210> SEQ ID NO 57
<211> LENGTH: 5
<212> TYPE: PRT
<213> ORGANISM: Artificial
```

```
<220> FEATURE:
<223> OTHER INFORMATION: metallopeptide derived from bombesin analog

<400> SEQUENCE: 57

Ala Val Cys His Leu
1               5

<210> SEQ ID NO 58
<211> LENGTH: 6
<212> TYPE: PRT
<213> ORGANISM: Artificial
<220> FEATURE:
<223> OTHER INFORMATION: metallopeptide derived from bombesin analog

<400> SEQUENCE: 58

Gln Trp Ala Val Cys His
1               5

<210> SEQ ID NO 59
<211> LENGTH: 5
<212> TYPE: PRT
<213> ORGANISM: Artificial
<220> FEATURE:
<223> OTHER INFORMATION: metallopeptide derived from bombesin analog

<400> SEQUENCE: 59

Trp Ala Val Cys His
1               5

<210> SEQ ID NO 60
<211> LENGTH: 4
<212> TYPE: PRT
<213> ORGANISM: Artificial
<220> FEATURE:
<223> OTHER INFORMATION: metallopeptide derived from bombesin analog

<400> SEQUENCE: 60

Ala Val Cys His
1

<210> SEQ ID NO 61
<211> LENGTH: 5
<212> TYPE: PRT
<213> ORGANISM: Artificial
<220> FEATURE:
<223> OTHER INFORMATION: metallopeptide derived from bombesin analog

<400> SEQUENCE: 61

Gln Trp Ala Val Cys
1               5

<210> SEQ ID NO 62
<211> LENGTH: 4
<212> TYPE: PRT
<213> ORGANISM: Artificial
<220> FEATURE:
<223> OTHER INFORMATION: metallopeptide derived from bombesin analog

<400> SEQUENCE: 62

Trp Ala Val Cys
1

<210> SEQ ID NO 63
<211> LENGTH: 4
<212> TYPE: PRT
<213> ORGANISM: Artificial
<220> FEATURE:
```

```
<223> OTHER INFORMATION: Alpha-MSH message segment

<400> SEQUENCE: 63

His Phe Arg Trp
1

<210> SEQ ID NO 64
<211> LENGTH: 11
<212> TYPE: PRT
<213> ORGANISM: Artificial
<220> FEATURE:
<223> OTHER INFORMATION: metallopeptide derived from melanocortin
      receptor binding compound
<220> FEATURE:
<221> NAME/KEY: MISC_FEATURE
<222> LOCATION: (3)..(3)
<223> OTHER INFORMATION: Norleucine

<400> SEQUENCE: 64

Tyr Val Xaa Gly His Cys Arg Trp Asx Arg Phe
1               5                   10

<210> SEQ ID NO 65
<211> LENGTH: 14
<212> TYPE: PRT
<213> ORGANISM: Artificial
<220> FEATURE:
<223> OTHER INFORMATION: Bombesin analog
<220> FEATURE:
<221> NAME/KEY: MISC_FEATURE
<222> LOCATION: (1)..(1)
<223> OTHER INFORMATION: Pyroglutamic acid

<400> SEQUENCE: 65

Xaa Gln Arg Leu Gly Asn Gln Trp Ala Val Gly His Leu Leu
1               5                   10

<210> SEQ ID NO 66
<211> LENGTH: 14
<212> TYPE: PRT
<213> ORGANISM: Artificial
<220> FEATURE:
<223> OTHER INFORMATION: Bombesin analog
<220> FEATURE:
<221> NAME/KEY: MISC_FEATURE
<222> LOCATION: (1)..(1)
<223> OTHER INFORMATION: Pyroglutamic acid

<400> SEQUENCE: 66

Xaa Gln Lys Leu Gly Asn Gln Trp Ala Val Gly His Leu Met
1               5                   10

<210> SEQ ID NO 67
<211> LENGTH: 14
<212> TYPE: PRT
<213> ORGANISM: Artificial
<220> FEATURE:
<223> OTHER INFORMATION: Bombesin analog
<220> FEATURE:
<221> NAME/KEY: MISC_FEATURE
<222> LOCATION: (1)..(1)
<223> OTHER INFORMATION: Pyroglutamic acid

<400> SEQUENCE: 67

Xaa Gln Arg Trp Gly Asn Gln Trp Ala Val Gly His Leu Met
1               5                   10

<210> SEQ ID NO 68
<211> LENGTH: 7
```

```
<212> TYPE: PRT
<213> ORGANISM: Artificial
<220> FEATURE:
<223> OTHER INFORMATION: Bombesin analog

<400> SEQUENCE: 68

Trp Ala Val Gly His Leu Met
1               5

<210> SEQ ID NO 69
<211> LENGTH: 50
<212> TYPE: PRT
<213> ORGANISM: Homo sapiens

<400> SEQUENCE: 69

Ser Ser Arg Arg Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
            20                  25                  30

Ala Phe Cys Tyr Cys Arg Lys Leu Gly Thr Ala Met Asn Pro Cys Ser
        35                  40                  45

Arg Thr
    50

<210> SEQ ID NO 70
<211> LENGTH: 46
<212> TYPE: PRT
<213> ORGANISM: Homo sapiens

<400> SEQUENCE: 70

Cys Val Arg Leu His Glu Ser Cys Leu Gly Gln Gln Val Pro Cys Cys
1               5                   10                  15

Asp Pro Cys Ala Thr Cys Tyr Cys Arg Phe Phe Asn Ala Phe Cys Tyr
            20                  25                  30

Cys Arg Lys Leu Gly Thr Ala Met Asn Pro Cys Ser Arg Thr
        35                  40                  45

<210> SEQ ID NO 71
<211> LENGTH: 13
<212> TYPE: PRT
<213> ORGANISM: Artificial
<220> FEATURE:
<223> OTHER INFORMATION: alpha-MSH analog specific for melanocortin
      receptors

<400> SEQUENCE: 71

Ser Tyr Ser Met Glu His Phe Arg Trp Gly Lys Pro Val
1               5                   10

<210> SEQ ID NO 72
<211> LENGTH: 14
<212> TYPE: PRT
<213> ORGANISM: Artificial
<220> FEATURE:
<223> OTHER INFORMATION: Bombesin analog derived from amphibian skin
<220> FEATURE:
<221> NAME/KEY: MISC_FEATURE
<222> LOCATION: (1)..(1)
<223> OTHER INFORMATION: Pyroglutamic acid

<400> SEQUENCE: 72

Xaa Gln Arg Leu Gly Asn Gln Trp Ala Val Gly His Leu Met
1               5                   10
```

METALLOPEPTIDE COMPOUNDS

CROSS-REFERENCE TO RELATED APPLICATIONS

This application is a continuation-in-part of U.S. patent application Ser. No. 10/769,695, entitled Knockout Identification Of Target-Specific Sites In Peptides, filed on Jan. 30, 2004, which in turn claims priority to and the benefit of the filing of U.S. Provisional Patent Application Ser. No. 60/444,129, entitled Knockout Identification Of Target-Specific Sites In Peptides, filed on Jan. 31, 2003, and the specification thereof of each is incorporated herein by reference.

This application is also a continuation-in-part of U.S. patent application Ser. No. 10/464,117, entitled Identification of Target-Specific Folding Sites in Peptides and Proteins, filed on Jun. 17, 2003, which is a continuation-in-part of PCT/US01/50075, entitled Identification of Target-Specific Folding Sites in Peptides and Proteins, filed on Dec. 19, 2001, which in turn claims priority to and the benefit of the filing of U.S. Provisional Patent Application Ser. No. 60/256,842, entitled Iterative Deconvolution Of Target-Specific Folding Sites In Peptides, filed on Dec. 19, 2000, U.S. Provisional Patent Application Ser. No. 60/304,835, entitled Metallopeptides for Treatment of Alzheimer's and Prion Disease, filed on Jul. 11, 2001, and U.S. Provisional Patent Application Ser. No. 60/327,835, entitled Urokinase-Type Plasminogen Activator Receptor Specific Metallopeptides, filed on Oct. 4, 2001, and the specification thereof of each is incorporated herein by reference.

This application claims priority to and the benefit of the filing of U.S. Provisional Patent Application Ser. No. 60/590,933, entitled Metallopeptide Compounds, filed on Jul. 23, 2004, and the specification thereof is incorporated herein by reference.

BACKGROUND OF THE INVENTION

1. Field of the Invention (Technical Field)

The present invention relates to metallopeptides that bind to a target of interest and are agonists, antagonists or mixed agonist-antagonists, and more particularly to biologically active metallopeptides derived from biologically active known peptide sequences, including compounds specific for one or more melanocortin receptors and bombesin analogs.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Metallopeptides. Specific metallopeptides and methods for making and using receptor-specific metallopeptides are generally disclosed in International Patent Application Serial No. PCT/US02/04431, entitled Melanocortin Metallopeptides for Treatment of Sexual Dysfunction, filed Feb. 13, 2002; International Patent Application Serial No. PCT/US01/50075, entitled Identification of Target-Specific Folding Sites in Peptides and Proteins, filed Dec. 19, 2001; International Patent Application Serial No. PCT/US00/16396, entitled Melanocortin Metallopeptide Constructs, Combinational Libraries and Applications, filed Jun. 14, 2000; International Patent Application Serial No. PCT/US99/29743, entitled Metallopeptide Combinatorial Libraries and Applications, filed Dec. 14, 1999; U.S. Pat. No. 6,027,711 entitled Structurally Determined Metallo-Constructs and Applications, issued Feb. 22, 2000; U.S. Pat. No. 6,331,285 entitled Structurally Determined Cyclic Metallo-Constructs and Applications, issued Dec. 18, 2001; and U.S. Pat. No. 5,891,418, entitled Peptide—Metal Ion Pharmaceutical Constructs and Applications, issued Apr. 6, 1999, and the specifications thereof of each are incorporated herein by reference. In summary, the foregoing patents and applications teach metallopeptide compositions and methods of making and using metallopeptides, which metallopeptides are mimics of turn structures, bind to receptors of interest, and are agonists, antagonists, or mixed agonist-antagonists. In one simplified embodiment, an amino acid sequence provides an $N_3S_1$ ligand for a tetradentate metal ion such as rhenium (Re). The tri-peptide metal ion binding sequence can include amino acids in the L- or D-configuration, which may further have modified or unnatural side chains. The metallopeptides can include one or more amino acid residues, mimetics or other structures at either or both ends, and any terminal or capping group. Such a metallopeptide has the following general structure:

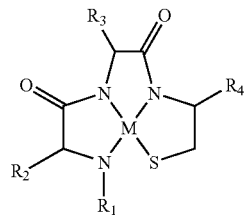

where $R_1$ and $R_4$ are the same or different and are independently selected from any terminal or capping group and optionally any one or more natural or unnatural L- or D-amino acid residues; $R_2$ and $R_3$ are the same or different and independently selected from any amino acid side chain moiety or derivative thereof; and M is a metal ion, such as Re.

Melanocortin. A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, mid-brain and brainstem, and melanocortin-5 receptors (MC5-R), expressed in a wide distribution of peripheral tissues.

In general, compounds specific for MC1-R are believed to be useful for treatment of melanoma, including use as radiotherapeutic or drug delivery agent, and as diagnostic imaging agents, particularly when labeled with a diagnostic radioisotope. Compounds specific for MC3-R, MC4-R or MC5-R are believed to be useful in-regulation of energy homeostasis, including use as agents for attenuating food intake and body weight gain, for use in treatment of anorexia, as a weight gain aid, for treatment of obesity, and other treatment of other food intake and metabolism-related purposes. Compounds specific for MC3-R and MC4-R, among other melanocortin receptors, can be used as agents for treatment of sexual dysfunction, including male erectile dysfunction. Compounds specific for MC3-R and MC4-R, among other melanocortin receptors, can be used to regulate blood pressure, heart rate and other neurophysiologic parameters. Other melanocortin receptor-specific compounds, such as MCR-1 agonists, can be used as tanning agents to increase melanin production. Compounds specific for MCR-1 and MCR-3 may be useful in regulation of inflammatory processes.

There is a significant need for compounds with high specificity for discrete melanocortin receptors, as well as compounds that are either agonists or antagonists for specific melanocortin receptors. High affinity compounds for melanocortin receptors can be used to exploit varied physiological responses associated with the melanocortin receptors, either as agonists or antagonists. In addition, melanocortin receptors have an effect on the activity of various cytokines, and high affinity compounds for melanocortin receptors can be used to regulate cytokine activity.

Bombesin. There is further a need for compounds that mimic bombesin analogs. Such compounds can be used in cancer diagnosis and therapy and a variety of physiological responses associated with bombesin receptors, including neurological and CNS responses, such as stroke, ischemia, head injury, and learning, memory and attention disorders.

Peptides, particularly peptides consisting entirely or primarily of L-isomer natural amino acids, are subject to peptidase and other enzymatic degradation, and typically have a very short half-life in vivo. There is a need for constructs made of amino acids but which are not susceptible to peptidase and other enzymatic degradation, or have decreased susceptibility to such degradation. The metallopeptide constructs of this invention advantageously are not subject to degradation, or have decreased susceptibility, and in most instances are excreted intact.

BRIEF SUMMARY OF THE INVENTION

In one embodiment the invention provides a metallopeptide comprising a biologically active alpha-melanocyte stimulating hormone (α-MSH), gamma-melanocyte stimulating hormone (γ-MSH), or bombesin sequence of length n residues, wherein a residue comprising a nitrogen atom and sulfur atom each available for complexation to a metal ion is inserted at any position from between the two and three position to the C-terminus side of the n position, with a metal ion complexed thereto, wherein any proline (Pro) residue which is either of the two residues on the immediately adjacent N-terminus side of the inserted residue comprising a nitrogen atom and sulfur atom available for complexation to a metal ion is substituted with a homolog. In one embodiment the metal ion is rhenium.

Thus the metallopeptide may be one wherein the α-MSH sequence is Ac-Ser-Tyr-Ser-Nle-Glu-His-Phe-Arg-Trp-Gly-Lys-Pro-Val-NH$_2$ (SEQ ID NO:1). In this embodiment, the residue comprising a nitrogen and sulfur atom may be L-Cys and the metallopeptide sequence may be selected from the group consisting of:

```
Ac-Ser-Tyr-Ser-Nle-Glu-His-Phe-Arg-Trp-Gly-Lys-Gly-Val-Cys-NH₂,   (SEQ ID NO:2)

Ac-Ser-Tyr-Ser-Nle-Glu-His-Phe-Arg-Trp-Gly-Lys-Gly-Cys-Val-NH₂,   (SEQ ID NO:3)

Ac-Ser-Tyr-Ser-Nle-Glu-His-Phe-Arg-Trp-Gly-Lys-Cys-Pro-Val-NH₂,   (SEQ ID NO:4)

Ac-Ser-Tyr-Ser-Nle-Glu-His-Phe-Arg-Trp-Gly-Cys-Lys-Pro-Val-NH₂,   (SEQ ID NO:5)

Ac-Ser-Tyr-Ser-Nle-Glu-His-Phe-Arg-Trp-Cys-Gly-Lys-Pro-Val-NH₂,   (SEQ ID NO:6)

Ac-Ser-Tyr-Ser-Nle-Glu-His-Phe-Arg-Cys-Trp-Gly-Lys-Pro-Val-NH₂,   (SEQ ID NO:7)

Ac-Ser-Tyr-Ser-Nle-Glu-His-Phe-Cys-Arg-Trp-Gly-Lys-Pro-Val-NH₂,   (SEQ ID NO:8)

Ac-Ser-Tyr-Ser-Nle-Glu-His-Cys-Phe-Arg-Trp-Gly-Lys-Pro-Val-NH₂,   (SEQ ID NO:9)

Ac-Ser-Tyr-Ser-Nle-Glu-Cys-His-Phe-Arg-Trp-Gly-Lys-Pro-Val-NH₂,   (SEQ ID NO:10)

Ac-Ser-Tyr-Ser-Nle-Cys-Glu-His-Phe-Arg-Trp-Gly-Lys-Pro-Val-NH₂,   (SEQ ID NO:11)

Ac-Ser-Tyr-Ser-Cys-Nle-Glu-His-Phe-Arg-Trp-Gly-Lys-Pro-Val-NH₂,   (SEQ ID NO:12)
or

Ac-Ser-Tyr-Cys-Ser-Nle-Glu-His-Phe-Arg-Trp-Gly-Lys-Pro-Val-NH₂.   (SEQ ID NO: 13)
```

In another embodiment the residue comprising a nitrogen and sulfur atom is D-Cys and the metallopeptide sequence is selected from the group consisting of:

```
Ac-Ser-Tyr-Ser-Nle-Glu-His-Phe-Arg-Trp-Gly-Lys-Gly-Val-D-Cys-NH₂,

Ac-Ser-Tyr-Ser-Nle-Glu-His-Phe-Arg-Trp-Gly-Lys-Gly-D-Cys-Val-NH₂,

Ac-Ser-Tyr-Ser-Nle-Glu-His-Phe-Arg-Trp-Gly-Lys-D-Cys-Pro-Val-NH₂,

Ac-Ser-Tyr-Ser-Nle-Glu-His-Phe-Arg-Trp-Gly-D-Cys-Lys-Pro-Val-NH₂,

Ac-Ser-Tyr-Ser-Nle-Glu-His-Phe-Arg-Trp-D-Cys-Gly-Lys-Pro-Val-NH₂,

Ac-Ser-Tyr-Ser-Nle-Glu-His-Phe-Arg-D-Cys-Trp-Gly-Lys-Pro-Val-NH₂,
```

```
                                        -continued
Ac-Ser-Tyr-Ser-Nle-Glu-His-Phe-D-Cys-Arg-Trp-Gly-Lys-Pro-Val-NH₂, Ac-Ser-Tyr-Ser-Nle-Glu-His-D-Cys-Phe-Arg-Trp-Gly-Lys-Pro-Val-NH₂, Ac-Ser-Tyr-Ser-Nle-Glu-D-Cys-His-Phe-Arg-Trp-Gly-Lys-Pro-Val-NH₂, Ac-Ser-Tyr-Ser-Nle-D-Cys-Glu-His-Phe-Arg-Trp-Gly-Lys-Pro-Val-NH₂, Ac-Ser-Tyr-Ser-D-Cys-Nle-Glu-His-Phe-Arg-Trp-Gly-Lys-Pro-Val-NH₂,
or Ac-Ser-Tyr-D-Cys-Ser-Nle-Glu-His-Phe-Arg-Trp-Gly-Lys-Pro-Val-NH₂.
```

The γ-MSH sequence may be Tyr-Val-Nle-Gly-His-D-Phe-Arg-Trp-Asp-Arg-Phe-NH₂. The metallopeptide may thus be one wherein the residue comprising a nitrogen and sulfur atom is L-Cys and the metallopeptide sequence is selected from the group consisting of:

```
                                                                            (SEQ ID NO:14)
Tyr-Val-Nle-Gly-His-D-Phe-Arg-Trp-Asp-Arg-Phe-Cys-NH₂,

Tyr-Val-Nle-Gly-His-D-Phe-Arg-Trp-Asp-Arg-Cys-Phe-NH₂,

Tyr-Val-Nle-Gly-His-D-Phe-Arg-Trp-Asp-Cys-Arg-Phe-NH₂,

Tyr-Val-Nle-Gly-His-D-Phe-Arg-Trp-Cys-Asp-Arg-Phe-NH₂,

Tyr-Val-Nle-Gly-His-D-Phe-Arg-Cys-Trp-Asp-Arg-Phe-NH₂,

Tyr-Val-Nle-Gly-His-D-Phe-Cys-Arg-Trp-Asp-Arg-Phe-NH₂,

Tyr-Val-Nle-Gly-His-Cys-D-Phe-Arg-Trp-Asp-Arg-Phe-NH₂,

Tyr-Val-Nle-Gly-His-Cys-D-Phe-Arg-Trp-Asp-Arg-Phe-NH₂,

Tyr-Val-Nle-Gly-Cys-His-D-Phe-Arg-Trp-Asp-Arg-Phe-NH₂,

Tyr-Val-Nle-Cys-Gly-His-D-Phe-Arg-Trp-Asp-Arg-Phe-NH₂,
or

Tyr-Val-Cys-Nle-Gly-His-D-Phe-Arg-Trp-Asp-Arg-Phe-NH₂.
```

The γ-MSH sequence may be Tyr-Val-Nle-Gly-His-D-Phe-Arg-Trp-Asp-Arg-Phe-NH₂ (SEQ ID NO:14). The metallopeptide may thus be one wherein the residue comprising a nitrogen and sulfur atom is L-Cys and the metallopeptide sequence is selected from the group consisting of:

```
Tyr-Val-Nle-Gly-His-Phe-Arg-Trp-Asp-Arg-Phe-Cys-NH₂,   (SEQ ID NO:15)

Tyr-Val-Nle-Gly-His-Phe-Arg-Trp-Asp-Arg-Cys-Phe-NH₂,   (SEQ ID NO:16)

Tyr-Val-Nle-Gly-His-Phe-Arg-Trp-Asp-Cys-Arg-Phe-NH₂,   (SEQ ID NO:17)

Tyr-Val-Nle-Gly-His-Phe-Arg-Trp-Cys-Asp-Arg-Phe-NH₂,   (SEQ ID NO:18)

Tyr-Val-Nle-Gly-His-Phe-Arg-Cys-Trp-Asp-Arg-Phe-NH₂,   (SEQ ID NO:19)

Tyr-Val-Nle-Gly-His-Phe-Cys-Arg-Trp-Asp-Arg-Phe-NH₂,   (SEQ ID NO:20)

Tyr-Val-Nle-Gly-His-Cys-Phe-Arg-Trp-Asp-Arg-Phe-NH₂,   (SEQ ID NO:21)

Tyr-Val-Nle-Gly-Cys-His-Phe-Arg-Trp-Asp-Arg-Phe-NH₂,   (SEQ ID NO:22)

Tyr-Val-Nle-Cys-Gly-His-Phe-Arg-Trp-Asp-Arg-Phe-NH₂,   (SEQ ID NO:23)
or

Tyr-Val-Cys-Nle-Gly-His-Phe-Arg-Trp-Asp-Arg-Phe-NH₂.   (SEQ ID NO:24)
```

The bombesin sequence may be Pyr-Gln-Arg-Leu-Gly-Asn-Gln-Trp-Ala-Val-Gly-His-Leu-Nle-NH₂ (SEQ ID NO:25). The metallopeptide may thus be one wherein the residue comprising a nitrogen and sulfur atom is L-Cys and the metallopeptide sequence is selected from the group consisting of:

```
Pyr-Gln-Arg-Leu-Gly-Asn-Gln-Trp-Ala-Val-Gly-His-Leu-Nle-Cys-NH₂,      (SEQ ID NO:26)
Pyr-Gln-Arg-Leu-Gly-Asn-Gln-Trp-Ala-Val-Gly-His-Leu-Cys-Nle-NH₂,      (SEQ ID NO:27)
Pyr-Gln-Arg-Leu-Gly-Asn-Gln-Trp-Ala-Val-Gly-His-Cys-Leu-Nle-NH₂,      (SEQ ID NO:28)
Pyr-Gln-Arg-Leu-Gly-Asn-Gln-Trp-Ala-Val-Gly-Cys-His-Leu-Nle-NH₂,      (SEQ ID NO:29)
Pyr-Gln-Arg-Leu-Gly-Asn-Gln-Trp-Ala-Val-Cys-Gly-His-Leu-Nle-NH₂,      (SEQ ID NO:30)
Pyr-Gln-Arg-Leu-Gly-Asn-Gln-Trp-Ala-Cys-Val-Gly-His-Leu-Nle-NH₂,      (SEQ ID NO:31)
Pyr-Gln-Arg-Leu-Gly-Asn-Gln-Trp-Cys-Ala-Val-Gly-His-Leu-Nle-NH₂,      (SEQ ID NO:32)
Pyr-Gln-Arg-Leu-Gly-Asn-Gln-Cys-Trp-Ala-Val-Gly-His-Leu-Nle-NH₂,      (SEQ ID NO:33)
Pyr-Gln-Arg-Leu-Gly-Asn-Cys-Gln-Trp-Ala-Val-Gly-His-Leu-Nle-NH₂,      (SEQ ID NO:34)
Pyr-Gln-Arg-Leu-Gly-Cys-Asn-Gln-Trp-Ala-Val-Gly-His-Leu-Nle-NH₂,      (SEQ ID NO:35)
Pyr-Gln-Arg-Leu-Cys-Gly-Asn-Gln-Trp-Ala-Val-Gly-His-Leu-Nle-NH₂,      (SEQ ID NO:36)
Pyr-Gln-Arg-Cys-Leu-Gly-Asn-Gln-Trp-Ala-Val-Gly-His-Leu-Nle-NH₂,      (SEQ ID NO:37)
or
Ac-Ala-Gln-Cys-Arg-Leu-Gly-Asn-Gln-Trp-Ala-Val-Gly-His-Leu-Nle-NH₂.  (SEQ ID NO:38)
```

The bombesin sequence may also be is D-Phe-Gln-Trp-Ala-Val-Gly-His-Leu-Leu-NH₂. The metallopeptide may thus be one wherein the residue comprising a nitrogen and sulfur atom is L-Cys and the metallopeptide sequence is selected from the group consisting of:

```
D-Phe-Gln-Trp-Ala-Val-Gly-His-Leu-Leu-Cys-NH₂,
D-Phe-Gln-Trp-Ala-Val-Gly-His-Leu-Cys-Leu-NH₂,
D-Phe-Gln-Trp-Ala-Val-Gly-His-Cys-Leu-Leu-NH₂,
D-Phe-Gln-Trp-Ala-Val-Gly-Cys-His-Leu-Leu-NH₂,
D-Phe-Gln-Trp-Ala-Val-Cys-Gly-His-Leu-Leu-NH₂,
D-Phe-Gln-Trp-Ala-Cys-Val-Gly-His-Leu-Leu-NH₂,
D-Phe-Gln-Trp-Cys-Ala-Val-Gly-His-Leu-Leu-NH₂,
or
D-Phe-Gln-Cys-Trp-Ala-Val-Gly-His-Leu-Leu-NH₂.
```

In another embodiment, the invention provides a metallopeptide comprising a biologically active α-MSH, γ-MSH, or bombesin sequence of length n residues, wherein a residue comprising a nitrogen atom and sulfur atom each available for complexation to a metal ion is substituted for the residue at any position from the three position to the n position, with a metal ion complexed thereto, wherein any Pro residue which is either of the two residues on the immediately adjacent N-terminus side of the substituent residue comprising a nitrogen atom and sulfur atom available for complexation to a metal ion is substituted with a homolog. The metal ion may be rhenium.

The γ-MSH sequence may be Tyr-Val-Nle-Gly-His-D-Phe-Arg-Trp-Asp-Arg-Phe-NH₂. The metallopeptide may thus be one wherein the residue comprising a nitrogen and sulfur atom is L-Cys and the metallopeptide sequence is selected from the group consisting of:

```
Tyr-Val-Nle-Gly-His-D-Phe-Arg-Trp-Asp-Arg-Cys-NH₂,
Tyr-Val-Nle-Gly-His-D-Phe-Arg-Trp-Asp-Cys-Phe-NH₂,
Tyr-Val-Nle-Gly-His-D-Phe-Arg-Trp-Cys-Arg-Phe-NH₂,
Tyr-Val-Nle-Gly-His-D-Phe-Arg-Cys-Asp-Arg-Phe-NH₂,
Tyr-Val-Nle-Gly-His-D-Phe-Cys-Trp-Asp-Arg-Phe-NH₂,
Tyr-Val-Nle-Gly-His-Cys-Arg-Trp-Asp-Arg-Phe-NH₂,
(SEQ ID NO:66)
Tyr-Val-Nle-Gly-Cys-D-Phe-Arg-Trp-Asp-Arg-Phe-NH₂,
Tyr-Val-Nle-Cys-His-D-Phe-Arg-Trp-Asp-Arg-Phe-NH₂,
or
Tyr-Val-Cys-Gly-His-D-Phe-Arg-Trp-Asp-Arg-Phe-NH₂.
```

The bombesin sequence may be Pyr-Gln-Arg-Leu-Gly-Asn-Gln-Trp-Ala-Val-Gly-His-Leu-Nle-NH₂ (SEQ ID NO:25). The metallopeptide may thus be one wherein the residue comprising a nitrogen and sulfur atom is L-Cys and the metallopeptide sequence is selected from the group consisting of:

```
Pyr-Gln-Arg-Leu-Gly-Asn-Gln-Trp-Ala-Val-Gly-His-Leu-Cys-NH₂,      (SEQ ID NO:40)
Pyr-Gln-Arg-Leu-Gly-Asn-Gln-Trp-Ala-Val-Gly-His-Cys-Nle-NH₂,      (SEQ ID NO:41)
```

-continued

```
Pyr-Gln-Arg-Leu-Gly-Asn-Gln-Trp-Ala-Val-Gly-Cys-Leu-Nle-NH₂,     (SEQ ID NO:42)

Pyr-Gln-Arg-Leu-Gly-Asn-Gln-Trp-Ala-Val-Cys-His-Leu-Nle-NH₂,     (SEQ ID NO:43)

Pyr-Gln-Arg-Leu-Gly-Asn-Gln-Trp-Ala-Cys-Gly-His-Leu-Nle-NH₂,     (SEQ ID NO:44)

Pyr-Gln-Arg-Leu-Gly-Asn-Gln-Trp-Cys-Val-Gly-His-Leu-Nle-NH₂,     (SEQ ID NO:45)

Pyr-Gln-Arg-Leu-Gly-Asn-Gln-Cys-Ala-Val-Gly-His-Leu-Nle-NH₂,     (SEQ ID NO:46)

Pyr-Gln-Arg-Leu-Gly-Asn-Cys-Trp-Ala-Val-Gly-His-Leu-Nle-NH₂,     (SEQ ID NO:47)

Pyr-Gln-Arg-Leu-Gly-Cys-Gln-Trp-Ala-Val-Gly-His-Leu-Nle-NH₂,     (SEQ ID NO:48)

Pyr-Gln-Arg-Leu-Cys-Asn-Gln-Trp-Ala-Val-Gly-His-Leu-Nle-NH₂,     (SEQ ID NO:49)

Pyr-Gln-Arg-Cys-Gly-Asn-Gln-Trp-Ala-Val-Gly-His-Leu-Nle-NH₂,     (SEQ ID NO:50)
or

Ac-Ala-Gln-Cys-Leu-Gly-Asn-Gln-Trp-Ala-Val-Gly-His-Leu-Nle-NH₂. (SEQ ID NO:51)
```

The bombesin sequence may be D-Phe-Gln-Trp-Ala-Val-Gly-His-Leu-Leu-NH₂. The metallopeptide may thus be one wherein the residue comprising a nitrogen and sulfur atom is L-Cys and the metallopeptide sequence is selected from the group consisting of:

```
D-Phe-Gln-Trp-Ala-Val-Gly-His-Leu-Cys-NH₂,

D-Phe-Gln-Trp-Ala-Val-Gly-His-Cys-Leu-NH₂,

D-Phe-Gln-Trp-Ala-Val-Gly-Cys-Leu-Leu-NH₂,

D-Phe-Gln-Trp-Ala-Val-Cys-His-Leu-Leu-NH₂,

D-Phe-Gln-Trp-Ala-Cys-Gly-His-Leu-Leu-NH₂,

D-Phe-Gln-Trp-Cys-Val-Gly-His-Leu-Leu-NH₂,
or

D-Phe-Gln-Cys-Ala-Val-Gly-His-Leu-Leu-NH₂.
```

In yet another embodiment the invention provides a bombesin metallopeptide consisting of a sequence selected from the group consisting of:

```
D-Phe-Gln-Trp-Ala-Val-D-Cys-His-Leu-Leu-NH₂,

D-Phe-Gln-Trp-Ala-Val-Cys-His-Leu-Leu-NH₂,
or

D-Phe-Gln-Trp-Cys-Val-Gly-His-Leu-Leu-NH₂,
``` with a metal ion complexed thereto.

It is a primary object of this invention to provide metallopeptide constructs, wherein the metallopeptides include a metal ion-complexing domain, such that a specific conformational secondary structural motif is obtained upon metal complexation.

Another object of this invention to provide metallopeptide constructs that form a surrogate for naturally-occurring structural motifs, such as those motifs commonly found in naturally-occurring peptides and proteins, including reverse turn structures, type I, II and III beta turns, gamma turns, inverse gamma turns, and short helical, sheet and extended chain structures. A secondary structural motif is necessarily defined by a conformationally-contrained metallopeptide, which secondary structural motif mimics, or can be made to mimic, the topologies found in naturally occurring structural motifs.

Another object of this invention is to provide metallopeptide constructs that include a ring structure that positions amino acid residues, amino acid side chain moieties and derivatives thereof in stereochemical space mimicking a naturally occurring reverse turn structure.

Another object of this invention is to provide metallopeptide constructs, wherein each metallopeptide includes a metal ion-complexing domain in a distinct, known and different location within the sequence, wherein the metallopeptides may be exposed to a substance and one or more metallopeptides will exhibit decreased specificity and/or affinity for the substance.

Another object of this invention is to provide methods for synthesis of peptides wherein the peptides contain a single reactive —SH group forming a part of a metal ion-complexing domain, whereby the reactive —SH group is protected during synthesis, and is deprotected only upon complexing the peptide with a metal ion.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

Certain terms as used throughout the specification and claims are defined as follows:

The terms “bind,” “binding,” “label,” “labeling,” “complex,” and “complexing,” as used throughout the specification and claims are generally intended to cover all types of physical and chemical binding, reactions, complexing, attraction, chelating and the like.

The “polypeptides” and “peptides” of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing polypeptides or peptides.

The term “polypeptide” as used throughout the specification and claims is intended to include any structure comprised of two or more amino acid residues, including chemical modifications and derivatives of amino acid residues. The term "polypeptides" thus includes a conventional "peptide" containing from two to about 20 amino acid residues, a conventional polypeptide with from about 20 to about 50 amino acid residues, and a conventional "protein" with a minimum of about fifty 50 amino acid residues. For the most part, the polypeptides made according to this invention and utilized as metallopeptides comprise fewer than 100 amino acid residues, and preferably fewer than 60 amino acid residues, and most preferably ranging from about 5 to 20 amino acid residues. The amino acid residues forming all or a part of a polypeptide may be naturally occurring amino acid residues, stereoisomers and modifications of such amino acid residues, non-protein amino acid residues, post-translationally modified amino acid residues, enzymatically modified amino acid residues, constructs or structures designed to mimic amino acid residues, and the like, so that the term "polypeptide" includes pseudopeptides and peptidomimetics, including structures which have a non-peptidic backbone. A "manufactured" peptide or polypeptide includes a peptide or polypeptide produced by chemical synthesis, recombinant DNA technology, biochemical or enzymatic fragmentation of larger molecules, combinations of the foregoing or, in general, made by any other method.

The "amino acid" and "amino acids" used in this invention, and the terms as used in the specification and claims, include the known naturally occurring protein amino acids, which are referred to by both their common three letter abbreviation and single letter abbreviation. See generally *Synthetic Peptides: A User's Guide*, G A Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference.

The term "amino acid side chain moiety" used in this invention includes any side chain of any amino acid, as the term "amino acid" is defined herein, including any derivative of an amino acid side chain moiety, as the term "derivative" is defined herein. Therefore, this includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, and saturated or unsaturated alkyl, aryl or aralkyl moieties.

A single amino acid residue, or a derivative thereof, is sometimes referred to herein as a "residue" or as an "amino acid." In addition, the following abbreviations have the meanings giving:

Ac—acetyl
D-Phe—D-phenylalanine
Pyr—pyroglutamic acid

Conventional amino acid residues have their conventional meaning as given in Chapter 2400 of the *Manual of Patent Examining Procedure*, $8^{th}$ Ed. Thus, "Nle" is norleucine, "Asp" is aspartic acid, "His" is histidine, "D-Phe" is D-phenylalanine, "Arg" is arginine, "Trp" is tryptophan, "Lys" is lysine, "Gly" is glycine, "Pro" is proline, "Tyr" is tyrosine, "Ser" is serine and so on.

The term "homolog" includes, without limitation, (a) a D-amino acid residue or side chain substituted for an L-amino acid residue side chain, (b) a post-translationally modified residue or side chain substituted for the residue or side chain, (c) a non-protein or other modified amino acid residue or side chain based on another such residue or side chain, such as phenylglycine, homophenylalanine, ring-substituted halogenated, and alkylated or arylated phenylalanines for a phenylalanine residue, diamino propionic acid, diamino butyric acid, ornithine, lysine and homoarginine for an arginine residue, and the like, and (d) any amino acid residue or side chain, coded or otherwise, or a construct or structure that mimics an amino acid residue or side chain, and which has at least a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

The term "acyl" includes a group RCO—, where R is an organic group. An example is the acetyl group $CH_3CO$—.

A group or aliphatic moiety is "acylated" when an alkyl or substituted alkyl group as defined above is bonded through one or more carbonyl [—(C=O)—] groups.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a metallopeptide of the present invention and one or more pharmaceutically acceptable carriers, and optionally one or more pharmaceutically active ingredients and agents.

As used herein, "parent polypeptide" refers to any sequence of amino acid residues that exhibits interaction, such as binding, to a target substance, and which may thus constitute a peptide, a polypeptide or a protein. The parent polypeptide is generally a polypeptide as defined herein, with from about 5 to about 100 amino acid residues, but the term parent polypeptide can also include larger constructs, generally considered in the art to be large polypeptides or proteins. The parent polypeptide may be any sequence that exhibits binding to a receptor found on, for example, cells, tissues, organs or other biological materials. Examples of parent polypeptides include, without limitation, biologically active peptides, hormones, neurotransmitters, enzymes, antibodies and the like. Such parent polypeptides may transmit signals, directly or indirectly, as a result of binding to a receptor, and thus a parent polypeptide may be an agonist, an antagonist, or a mixed agonist-antagonist. Examples of suitable parent polypeptides of the invention include melanocortin-receptor specific peptides, bombesin, urokinase-type tissue plasminogen activator protein, amyloid beta-protein related peptides, prion disease related peptides, vasopressin peptides, oxytocin peptides, angiotensin peptides, calcitonin, calcitonin gene related peptide, bradykinin, cholecystokinin, urotensin, bombesin, neuromedin B, gastrin releasing peptide, atrial naturetic peptide, somatostatin, opioid peptides, human growth hormone, human prolactin receptor ligands, various interferons such as alpha-interferon, epidermal growth factor, tumor necrosis factor, and various hypotensive peptides, fibrinolytic peptides, chemotactic peptides, growth promoter peptides, mitogens, immunomodulators and the like.

A "biologically active" parent polypeptide is one which exhibits binding to or functionality with a receptor of interest, such as determined by a competitive inhibition or similar assay where the binding or functional activity is directly determined. In other embodiments other assays or tests may be employed. These assays may, but need not, be functional assays. Examples of assays include any of a variety of competitive inhibition assays, direct binding assays, functional assays, and the like. It is also possible and contemplated to employ assays that determine, for example, whether a construct of the invention is an agonist, antagonist or mixed agonist-antagonist, and further where binding and function can separately be determined, to independently determine receptor affinity and specificity as well as functional activity. Examples of such assays and tests are well known and well documented in the art. A "biologically active" parent peptide may be a full-length sequence as found endogenously in one or more species, may be a derivative which is a full-length sequence with one or more substitutions of one or more amino acid residues, may be a derivative which is a truncated or shortened version of a full-length sequence, or may be a derivative which is a truncated or shortened version of a full-length sequence with one or more substitutions of one or more amino acid residues.

By a melanocortin receptor "agonist" is meant an endogenous or drug substance or compound, including metallopeptides disclosed herein, that can interact with a melanocortin receptor and initiate a pharmacological response, including but not limited to adenylyl cyclase expression, characteristic of the melanocortin receptor. By a melanocortin receptor "antagonist" is meant a drug or a compound, including metallopeptides disclosed herein, that opposes the melanocortin receptor-associated responses normally induced by a melanocortin receptor agonist agent, but without it initiating a pharmacological response characteristic of the melanocortin receptor, such as increasing or decreasing adenylyl cyclase expression. By a melanocortin receptor "inverse agonist" is meant a drug or a compound, including metallopeptides disclosed herein, which is an antagonist with respect to an agonist, and which by itself induces or initiates a pharmacological response characteristic of the melanocortin receptor, such as reducing basal or constitutive adenylyl cyclase expression. By a melanocortin receptor "protean agonist" is meant a drug or a compound, including metallopeptides disclosed herein, which acts as either an inverse agonist or an agonist, depending on the constitutive activity of the MC4-R, either promoting a switch to a less active conformation or enriching the active conformation. In general, inverse and protean agonists are discussed at length in Kenakin, T. Inverse, protean, and ligand-selective agonism: matters of receptor conformation. *The FASEB Journal* 15:598-611, 2001, incorporated here by reference as if set forth in full.

By "α-MSH" is meant the peptide Ac-Ser-Tyr-Ser-Nle-Glu-His-Phe-Arg-Trp-Gly-Lys-Pro-Val-NH$_2$ (SEQ ID NO:1) and derivatives, analogs and homologs thereof, including without limitation NDP-α-MSH and Ac-Ser-Tyr-Ser-Met-Glu-His-Phe-Arg-Trp-Gly-Lys-Pro-Val-NH$_2$ (SEQ ID NO:71), the parent compound with a Met$^4$ which is substituted by a Nle$^4$ in SEQ ID NO:1.

By "NDP-α-MSH" is meant the peptide Ac-Ser-Tyr-Ser-Nle-Glu-His-D-Phe-Arg-Trp-Gly-Lys-Pro-Val-NH$_2$ and derivatives, analogs and homologs thereof.

By "γ-MSH" is meant the peptide Tyr-Val-Nle-Gly-His-Phe-Arg-Trp-Asp-Arg-Phe-NH$_2$ (SEQ ID NO:14) and derivatives, analogs and homologs thereof, including without limitation Tyr-Val-Nle-Gly-His-D-Phe-Arg-Trp-Asp-Arg-Phe-NH$_2$.

By "AgRP" is meant Agouti-related protein or a biologically active fragment of Agouti protein, and for applications relating to human AgRP, including the truncated variants AgRP (83-132) and AgRP (87-132). AgRP includes proteins or fragments thereof made by purification of biological materials, synthetic methodologies or recombinant methodologies, and includes the sequences and constructs, including analogs, homologs and variants thereof, disclosed generally in Yang, Y.-K., Thompson, D. A., Dickinson, C. J., Wilken, J., Barsh, G. S., Kent, S. B. H., Gantz, I. Characterization of agouti-related protein binding to melanocortin receptors. *Molecular Endocrinology* 13:148-155,1999; and Ollmann, M. M., Wilson, B. D., Yang, Y.-K., Kerns, J. A., Chen, Y. Gantz, I., Barsh, G. S. *Science* 278:135-138, 1997.

By "AgRP (83-132)" is meant a biologically active fragment of AgRP containing the amino acids at positions 83 to 132 of human AgRP (Ser-Ser-Arg-Arg-Cys-Val-Arg-Leu-His-Glu-Ser-Cys-Leu-Gly-Gln-Gln-Val-Pro-Cys-Cys-Asp-Pro-Cys-Ala-Thr-Cys-Tyr-Cys-Arg -Phe-Phe-Asn-Ala-Phe-Cys-Tyr-Cys-Arg-Lys-Leu-Gly-Thr-Ala-Met-Asn-Pro-Cys-Ser-Arg-Thr (SEQ ID NO:69). AgRP (83-132) is included within the definition of AgRP given here.

By "AgRP (87-132)" is meant a biologically active fragment of AgRP containing the amino acids at positions 87 to 132 of human AgRP (Cys-Val-Arg-Leu-His-Glu-Ser-Cys-Leu-Gly-Gln-Gln-Val-Pro-Cys-Cys-Asp-Pro-Cys-Ala-Thr-Cys-Tyr-Cys-Arg-Phe-Phe-Asn-Ala -Phe-Cys-Tyr-Cys-Arg-Lys-Leu-Gly-Thr-Ala-Met-Asn-Pro-Cys-Ser-Arg-Thr (SEQ ID NO: 70). AgRP (87-132) is included within the definition of AgRP given here.

By "bombesin" is meant the peptide Pyr-Gln-Arg-Leu-Gly-Asn-Gln-Trp-Ala-Val-Gly-His-Leu-Nle-NH$_2$ (SEQ ID NO:25) and derivatives, analogs and homologs thereof, including without limitation D-Phe-Gln-Trp-Ala-Val-Gly-His-Leu-Leu-NH$_2$; Pyr-Gln-Arg-Leu-Gly-Asn-Gln-Trp-Ala-Val-Gly-His-Leu-Leu-NH$_2$ (SEQ ID NO:65), including the peptide of SEQ ID NO:65 where there is a reduced peptide bond between Leu$^{13}$ and Leu$^{14}$, Pyr-Gln-Lys-Leu-Gly-Asn-Gln-Trp-Ala-Val-Gly-His-Leu-Met-NH$_2$ (SEQ ID NO:66), Pyr-Gln-Arg-Trp-Gly-Asn-Gln-Trp-Ala-Val-Gly-His-Leu-Met-NH$_2$ (SEQ ID NO:67), and Trp-Ala-Val-Gly-His-Leu-Met-NH$_2$ (SEQ ID NO:68), and analogs of the foregoing wherein the Met is substituted, such as with Nle, and Pyr-Gln-Arg-Leu-Gly-Asn-Gln-Trp-Ala-Val-Gly-His-Leu-Met-NH$_2$ (SEQ ID NO:72).

The constructs of this invention also include a "metal ion", which may be an ionic form of any element in metallic form, including but not limited to metals and metalloids. The metal ion may, but need not, be radioactive, paramagnetic or superparamagnetic. The metal ion can be of any oxidation state of any metal, including oxidation states of vanadium (V), manganese (Mn), iron (Fe), cobalt (Co), nickel (Ni), copper (Cu), zinc (Zn), gallium (Ga), arsenic (As), selenium (Se), yttrium (Y), molybdenum (Mo), technetium (Tc), ruthenium (Ru), rhodium (Rh), palladium (Pd), silver (Ag), cadmium (Cd), indium (In), tin (Sn), tungsten (W), rhenium (Re), osmium (Os), iridium (Ir), platinum (Pt), gold (Au), mercury (Hg), thallium (Tl), lead (Pb), bismuth (Bi), polonium (Po), astatine (At), samarium (Sm), europium (Eu), and gadolinium (Gd). The metal ion can also be a radionuclide of any of the foregoing, including In, Au, Ag, Hg, Tc, Re, Sn, At, Y and Cu. A preferred metal ion with a tetradentate coordination sphere is Re. For applications wherein a radioisotope is desirable for screening or in assay systems, an alpha-, gamma- or beta-emitting radionuclide may be employed.

During synthesis the —SH group of a cysteine residue may be protected using an orthogonal protecting agent as set forth below. The resulting orthogonally-protected Cys-containing peptide is then deprotected, and subsequently complexed with a metal ion, such as a rhenium ion, thereby forming a metallopeptide, using in the case of a rhenium ion a suitable pre-formed metal-oxo transfer agent, such as $Re(O)Cl_3(PPh_3)_2$.

In the event that the metallopeptide contains one or more endogenous Cys residues, it is possible to protect the intrinsic Cys residues with a non-orthogonal —SH protecting agent, to protect the introduced $N_1S_1$ residue with an orthogonal —SH protecting agent, to thereafter selectively deprotect the orthogonal —SH protecting agent, to then complex the deprotected $N_1S_1$ residue with a metal ion, and thereafter to deprotect the Cys residue with the non-orthogonal —SH protecting agent. Examples of common non-orthogonal —SH protecting groups include, but are not limited to, trityl, benzyl, p-methoxy benzyl, and $^tBu$.

In the event that the metallopeptide contains one or more Pro resides, any Pro in the two residues on the immediately adjacent amino-terminus side of the Cys that is subsequently complexed with a metal ion is located in a position that forms a part of the putative metal ion complexation tri-peptide sequence, and is conservatively substituted. Such substitution is required because there is no available N in Pro to complex to the coordination sphere of a metal ion, and therefore Pro cannot form a part of a metal ion complexation tri-peptide sequence. Accordingly, any such Pro may be substituted with Gly, Ala or Ser (among naturally occurring coded protein amino acid residues), and preferably Gly or Ala. In a further embodiment, any synthetic or unnatural relatively small, neutral amino acid may be employed, for example Aib, 1-amino, 1-cyclopentane carboxylic acid, or ΔAla.

The choice of metal ion partially determines the structure of the resulting turning structure. For example, use of a Re ion results in a square pyramidal coordination geometry. Tc (which has substantially similar coordination requirements and chemistries and generally may be substituted for Re in any example herein) similarly results in a square pyramidal coordination geometry. Use of other metal ions, such as Cu, Ni or Zn, results in square planar coordination geometries. Thus while the atomic radius of Re is on the order of 1.37 Å and that of Cu is smaller, on the order of 1.28 Å, the resulting dimensions of the metal coordination group is determined, in large part, by the coordination geometry, and not just by the atomic radius of the metal ion. With metal ions such as Cu, Ni or Zn employing square planar coordination tetradentate geometries, the metal ion and each of the four coordinating atoms (such as S, N or O) are co-planar. However, when employing metal ions such as Re or Tc (which result in square pyramidal coordination tetradentate geometries), the four coordinating atoms (such as S, N or O) are co-planar, but the metal ion is, in the case of Re, about 0.65 Å removed from the plane of the coordinating atoms.

In this invention any of a wide range of metal ions may be employed, but Re and Tc are particularly preferred. Both metals form similar complexes with Cys-containing peptides yielding similar square pyramidal complexes. Re-complexed peptides, however, are chemically more stable than the corresponding Tc-containing peptides. The square planar complexes of Zn and Cu, with the metal ion as well as the four coordinating atoms of the peptide all in one plane, results in a near identical complexation geometry as is obtained with Tc or Re, where the metal ion is projected upwards from the plane of four coordinating atoms of the peptide, notwithstanding the differences in the atomic radius of the metal ions. The net result are metallopeptides that each afford topographic similarities, whether for example Re, Tc, Zn or Cu is employed. The Re-complexed metallopeptides, however, are unique in that the metallopeptides are air and moisture stable, without any need for special or exotic excipients or protecting agents. The Re-complexes can routinely be isolated as solid compounds and are stable as solids and in solutions over a wide pH range, thereby facilitating both analytical characterization and, more importantly, use in both in vitro and in vivo biological experiments over a wide range of conditions. Other metal types, such as Zn-complexes and Cu-complexes, are utilized in experiments in a solution form. However, Zn-complexes and Cu-complexes are extremely easy to form, and essentially are formed in the presence of 1 micromolar to 1 millimolar concentration of the metal ion in an appropriately buffered solution.

The Re- and Tc-complexes are metaloxo complexes, generally and in a preferred embodiment in an oxidation state [V]. The metaloxo core M=O in the metallopeptides may give rise to an isomerism in the core structure. The metal-oxo group may be syn or anti with respect to a chiral amino acid side chain. Since the orientation of the oxo group does not alter the topographic surface created by the amino acid side chains, this isomerism has little or no effect on the biological activity of the metallopeptides. That is, the oxo group of a metal ion does not sterically hinder the conformationally constrained amino acid side chain presentations. In fact, the metal ion is situated at a location spatially similar to that where turns are stabilized by a hydrogen bond in natural turn structures; thus the oxo group falls within a space not addressable in natural turn structures. Computer modeling of individual syn- and anti-isomers of metallopeptides have shown that these two structures are completely indistinguishable with respect to each amino acid location, with orientation of the oxo group being the only difference.

It may be seen that in the practice of the invention a free thiol or sulfhydryl (—SH) group of a residue is utilized for complexation of metal ions. Peptides and other organic molecules with free —SH groups, however, are easily oxidized in air and in solution, and can often form a disulfide-linked dimer. If more than one free —SH group is present in a molecule, oxidation may lead to a complex polymer. In addition, with more than one free —SH group when the metal ion is complexed to the peptide, it is possible to have metal ion complexation at more than one site in the peptide. This results in mixed species of metallopeptides.

In order to construct metallopeptides of this invention which incorporate an —SH group it is desirable to employ S-protected derivatives. The S-protecting group is chosen such that (a) the synthesis of peptides with the S-protecting group is compatible with methods of solution and solid phase peptide synthesis, so that the S-protecting group is stable during synthetic procedures, and (b) the S-protecting group can be deprotected in situ, without cleavage from the resin in the case of solid phase synthesis, during the metal complexation step. An S-protecting group meeting the forgoing criteria is defined herein as an orthogonal S-protected group (OSPG). Many prior art protecting groups meet at most only one of the two criteria specified above, and thus do not constitute an OSPG as defined herein.

Use of orthogonally S-protected thiol groups permits synthesis of metallo-compounds in a single vessel. A mixture of compounds, each compound containing an OSPG, is used for complexation with a metal ion, and it is only during metal ion complexation that the S-protected group is deprotected, and accordingly polymerization and cross-linking is avoided. This procedure thus provides homogenous libraries of metallopeptides.

One OSPG meeting the criteria specified above, and which can be advantageously used in this invention, employs an S$^t$Bu (S-thio-butyl or S-t-butyl) group to protect the —SH group. The S$^t$Bu group is stable under both the acidic and basic conditions typically employed in peptide synthesis. Further, the S$^t$Bu group may be cleaved by reduction using a suitable phosphine reagent, which reduction step may be employed immediately prior to, or in conjunction with, complexing of a metal ion to the peptide. Such OSPG cleavage does not cleave the peptide from the resin, or otherwise alter the structure of the peptide.

Another OSPG meeting the criteria specified above and suitable for this invention employs an S-Acm (S-acetamidomethyl) group to protect the —SH group. The Acm group is also stable under the acid and base conditions usually employed during peptide synthesis. The S-Acm group may be removed by treatment of S-Acm-protected peptide or peptide resin with mercury (II) acetate or silver (I) tertrafluoroborate, which liberates the thiol peptide in its mercury or silver ion-complexed state. If a mercury or silver ion metallopeptide is desired, the resulting metallopeptide may be kept in solution and employed in assays as described herein. Alternatively, free thiol-containing peptide can be recovered by treating the mercury or silver ion and thiol complexed salts with an excess of a thiol-containing reagent, such as beta-mercaptoethanol or dithiothreitol. The resulting peptide is then used for metal complexation to a metal such as Re or Tc. Alternatively, the mercury or silver ion and thiol complexed peptide may be directly treated with a metal ion complexing reagent, such as an Re complexing reagent, to form a desired metallopeptide, such as an Re metallopeptide.

Other examples of OSPGs for metallopeptides include 4-methoxytrityl (Mmt), 3-nitro-2-pyridinesulfenyl (Npys) and S-sulfonate (SO$_3$H). Mmt is selectively removed upon treatment with 1% TFA in dichloromethane. Npys and S-sulfonate are selectively removed by treatment with a thiol-containing reagent such as beta-mercaptoethanol or dithiothreitol or a phosphine reagent such as tributyl phosphine. The Npys group (R G Simmonds et al: *Int J Peptide Protein Res*, 43:363, 1994) is compatible with Boc chemistry for peptide synthesis and the S-sulfonate (I Maugras et al: *Int J Peptide Protein Res*, 45:152, 1995) is compatible with both Fmoc and Boc chemistries. Similar OSPGs derived from homologous series of S-alkyl, or S-aryl, or S-aralkyl may also be used in this invention. A primary characterization of the OSPG is that its use results in the formation of a disulfide (S—S) bond utilizing one sulfur atom each from the thiol-containing amino acid and the protecting group. In addition, the resulting disulfide bond is cleavable by the use of any of a variety of disulfide cleaving agents, including but not limited to phosphine- and thiol-containing reagents.

The method employing S$^t$Bu protected —SH groups, or other OSPGs, may be employed for the generation of either solid phase or soluble libraries. For solid phase libraries, peptides may be synthesized by use of conventional Fmoc chemistry. In the case of conventional Fmoc chemistry, Fmoc-L-Cys-(S$^t$Bu) is coupled to an appropriate resin, via one or more intermediate amino acid residues, and additional amino acid residues are thereafter coupled to the L-Cys-(S$^t$Bu) residue. S$^t$Bu may be employed with either L- or D-Cys, and any of a variety of other amino acid residues, including designer or unnatural amino acid residues and mimics thereof, characterized by an —SH group available for complexation to a metal ion, including, but not limited to, 3-mercapto phenylananine and other related 3-mercapto amino acid residues such as 3-mercapto valine (penicillamine), all of the foregoing of which constitute an $N_1S_1$ residue. In all these cases, S-protection can be by S-Bu$^t$, S-Acm, Mmt, Npys, S-sulfonate and related groups, as described above.

The complexation of metal ions to the peptides is achieved by mixing the peptides with the metal ion. This is conveniently done in solution, with the solution including an appropriate buffer. In one approach the metal ion is, when mixed with the peptide or peptidomimetic constituents, already in the oxidation state most preferred for complexation. Some metal ions are complexed in their most stable oxidation state, such as calcium (II), potassium (I), indium (III), manganese (II), copper (II), zinc (II) and other metals. In other instances, the metal must be reduced to a lower oxidation state in order to be complexed. This is true of ferrous, ferric, stannous, stannic, technetiumoxo[V], pertechnetate, rheniumoxo[V], perrhenate and other similar metal ions. Reduction may be performed prior to mixing with the sequences, simultaneously with mixing with the sequences, or subsequent to mixing with the sequences. Any means of reduction of metal ions to the desired oxidation state known to the art may be employed.

Re and Tc are preferred metal ions to employ, particularly in that the resulting metallopeptides may be purified and removed from solution, such as by lyophilization, and remain stable. Other metallopeptides, as for example metallopeptides utilizing Zn, Cu, Ni, Co, Fe and Mn, are stable in solution, but are prone to oxidation and loss of the metal ion if removed from solution. Thus these metallopeptides must be kept in solution, and optimally at the appropriate pH and with appropriate buffers, at all times, including during conduct of assays and other tests. This imparts some limitations on the utility of these metal ions; however, metallopeptides utilizing metal ions other than Re or Tc may be employed as discussed herein.

Solid phase resin bound peptide or peptidomimetic sequences may be labeled with rhenium ion by treatment with the rhenium transfer agent ReOCl$_3$(PPh$_3$)$_2$ in the presence of a base, such as 1,8-diazabicyclo[5,4,0]undec-7-ene (DBU). The sequences may then be cleaved from the resin. Peptide or peptidomimetic sequences in solution may similarly be labeled by treatment with the rhenium transfer agent ReOCl$_3$(PPh$_3$)$_2$ in the presence of a base, such as triethyl amine, disopropylethylamine, N-methylmopholine or DBU.

Metal complexation in the presence of DBU as a base can conveniently be accomplished at ambient room temperature.

In an alternative method of metal complexation a mild base, such as sodium acetate, can be used. In this case the thiol-containing sequence, either in solution or bound to solid phase, is taken in a suitable solvent, such as dimethylformamide (DMF), dichloromethane (DCM), N-methylpyrrolidinone (NMP), methanol (MeOH) or a mixture thereof, and heated to 60-70° C. with the rhenium transfer agent $ReOCl_3(PPh_3)_2$ in the presence of sodium acetate for 15 minutes. Similarly, other bases such as triethylamine, ammonium hydroxide and so on, may be employed: According to this invention, MeOH is a preferred choice of solvent for rhenium complexation in the case of S-deprotected peptides in solution. The solvent choice for S-deprotected peptides still attached to the solid phase is guided mainly by considerations of superior solvation (swelling) of the solid phase. DMF and NMP may be employed. Various mixtures of these solvents, also in combination with MeOH, and DCM, $CHCl_3$ and so on, may also be employed to yield optimized complexation results.

In one embodiment of this invention, an $S^tBu$ protected peptide is treated in situ with rhenium transfer agent in the presence of DBU and tributylphosphine to effect S-deprotection and rhenium complexation in one vessel. Alternately, complexing of rhenium to the $S^tBu$ protected peptide in the presence of rhenium perrhenate may be accomplished by treatment with $Sn[II]Cl_2$. This reagent effects S-deprotection as well as conversion of the $ReO_4$ state to an ReO state in situ to thereby effect complexation of the rhenium to the S-deprotected peptide. A preferred procedure in this invention is the use of S—$Bu^t$ protected peptide with S-deprotection by treatment with tributylphosphine, and metal complexation of the resulting peptide utilizing $ReOCl_3(PPh_3)_2$ in the presence of DBU at room temperature.

In a preferred embodiment a solid-phase methodology is employed for the synthesis of metallopeptides, in which the metal ion complexation is also achieved while the peptide is on the solid phase. Using Fmoc chemistry a linear peptide is fully assembled on rink amide resin using a $S^tBu$ protected Cys derivative. Following synthesis of the peptide, the $S^tBu$ group is removed by treatment with $Bu_3P$ in DMF. The resulting free —SH containing peptide-resin is treated with the rhenium transfer reagent $ReO[V]Cl_3(PPh_3)_2$ in presence of DBU as base. Complete metal-ion complexation is achieved within 2 hours at room temperature. The resulting metallopeptide resin is washed, dried and then treated with TFA to cleave the metallopeptide from the resin and remove all side chain protecting groups. The metallopeptide is purified by HPLC and characterized by mass spectrometry and amino acid analysis.

Clinical Applications. The metallopeptides disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

According to one embodiment of the present invention, metallopeptides may be employed that are MC4-R agonists, partial agonists, antagonists, inverse agonists or functionally inactive. Such compounds may be used to treat sexual dysfunction, including male erectile dysfunction and female sexual dysfunction, to treat obesity and other energy homeostasis-related conditions, to treat cachexia and other wasting syndromes, and as otherwise described herein.

Melanocortin receptor-specific metallopeptides of this invention that are MC1-R specific can be used as chemoprevention agents against sun-induced, such as by UV radiation, neoplastic activity in human skin. MC1-R agonist metallopeptides of this invention may be employed to stimulate epidermal melanocytes to produce melanin as well as to convert pheomelanin to eumelanin. Eumelanin, which is dark brown or black pigmentation, is considered more photo-protective than pheomelanin, which is yellow or red pigmentation. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is proposed to result from the same pathway by local production of melanotropic peptide from a POMC gene in the epidermis. Thus stimulation of eumelanin production and conversion of pheomelanin to eumelanin may be a desirable chemoprevention modality in blocking sun- or UV-induced neoplastic activity in skin. A potent, high-affinity and highly selective MC1-R agonist metallopeptides of this invention can accordingly be used as a therapeutic chemoprevention agent for combating harmful sun or UV exposure that induces neoplastic activity in skin melanocytes.

In another embodiment, metallopeptides of this invention that are MC4-R agonists can be used as a therapeutic agent to modify energy metabolism and feeding behavior, including treatment of pathologic obesity and related conditions. Metallopeptides of this invention that are MC4-R antagonists can also be used as a therapeutic agent in eating disorders, such as treatment of anorexia and cachexia, which is malnutrition and wasting due to illness. Control centers for eating and satiety reside in the hypothalamus. These responses are determined by diverse hormones and soluble factors that signal through specific receptors in the hypothalamus. MC4-R is known-to be expressed in the brain, and inactivation of this receptor by gene targeting has resulted in mice with a maturity-onset obesity syndrome associated with hyperphagia, hyperinsulinemia and hyperglycemia.

In yet another embodiment, metallopeptides of this invention can be used as therapeutic agents for treatment of sexual dysfunction, including treatment of both male erectile dysfunction and female sexual dysfunction.

In yet another embodiment, metallopeptides of this invention may be used as therapeutic agents for treatment of inflammation, including specifically MC1-R, MC3-R and MC5-R agonists.

In yet another embodiment of the invention, metallopeptides of this invention that are MC5-R specific can be used as agents to decrease sebum production, and thus may be efficacious in the treatment of acne and related diseases. The metallopeptides for this application may be conveniently formulated for local administration, as through a gel, lotion, cream or other topical formulation.

Formulations. The metallopeptides may be formulated by any means known in the art, including but not limited to tablets, capsules, caplets, suspensions, powders, lyophilized forms and aerosols and may be mixed and formulated with buffers, binders, stabilizers, anti-oxidants and other agents known in the art. The metallopeptides may be administered by any systemic or partially systemic means known in the art, including but not limited to intravenous injection, subcutaneous injection, administration through mucous membranes, oral administration, dermal administration, skin patches, aerosols and the like.

One embodiment of the present invention provides a pharmaceutical composition that includes one or more metallopeptides disclosed herein and a pharmaceutically acceptable carrier. The metallopeptides may thus be formulated or compounded into pharmaceutical compositions that include at least one metallopeptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is suitable, and stabilizing agents, preservatives and solubilizing agents may also be employed. For solid administration formulations, any of a variety of thickening, filler, bulking and carrier additives may be employed, such as starches, sugars, fatty acids and the like. For pharmaceutical formulations, it is also contemplated that any of a variety of measured-release, slow-release or time-release formulations and additives may be employed, such that the dosage may be formulated so as to effect delivery of a metallopeptide of this invention over a period of time.

The metallopeptides of this invention may be in the form of any pharmaceutically acceptable salt. Acid addition salts of the metallopeptides of this invention are prepared in a suitable solvent from the metallopeptide and an excess of an acid, such as hydrochloric, hydrobromic, sulfuric, phosphoric, acetic, trifluoroacetic, maleic, succinic or methanesulfonic acids. The acetate salt form is especially useful. Where the metallopeptides of this invention include an acidic moiety, suitable pharmaceutically acceptable salts may include alkali metal salts, such as sodium or potassium salts, or alkaline earth metal salts, such as calcium or magnesium salts.

The metallopeptides disclosed herein and pharmaceutical compositions comprising such metallopeptide or metallopeptides, may be administered by injection, which injection may be intravenous, subcutaneous, intramuscular, intraperitoneal or by any other means known in the art. In general, any route of administration by which the metallopeptides of this invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

Therapeutically Effective Amount. In general, the actual quantity of metallopeptide administered to a patient will vary between fairly wide ranges depending upon the mode of administration, the formulation used, and the response desired. This may readily be determined by one of ordinary skill in the art through means such as pharmacokinetic studies, plasma half-life studies, dose escalation studies, and the like. The dosage for treatment is administration, by any of the foregoing means or any other means known in the art, of an amount sufficient to bring about the desired therapeutic effect. Thus a therapeutically effective amount includes an amount of a metallopeptide or pharmaceutical composition of this invention that is sufficient to induce the desired therapeutic effect.

The metallopeptides disclosed herein may be highly active. For example, a metallopeptide can be administered at 0.01, 0.05, 0.1, 0.5, 1, 5, 10, 50, 100, or 500 µg/kg body weight, depending on specific metallopeptide selected, the desired therapeutic response, the route of administration, the formulation and other factors known to those of skill in the art. Conventional dose response studies and other pharmacological means may be employed to determine the optimal dose for a desired effect with a given metallopeptide, given formulation and given route of administration.

Assays and Animal Models.

Selected metallopeptides are tested in melanocortin receptor-based assays to determine binding and functional status, and were tested in animal models of penile erection, feeding behavior and conditioned taste avoidance, as discussed below. The following assays and animal models are employed, with modifications as discussed in the examples.

Competitive inhibition assay using $[I^{125}]$-NDP-α-MSH. A competitive inhibition binding assay is conducted using membranes prepared from HEK-293 cells transfected to express hMC3-R, hMC4-R or hMC5-R, and from B-16 mouse melanoma cells (containing MC1-R) using 0.2 to 0.4 nM $[I^{125}]$-NDP-α-MSH (New England Nuclear) in 50 mM HEPES buffer containing 1 mM $MgCl_2$, 2 mM $CaCl_2$, and 5 mM KCl, at pH 7.2. In certain experiments, HEK-293 cells transfected to express hMC1-R are also employed. The assay tube also contains a chosen concentration of the test metallopeptide of this invention, typically a 1 mM concentration, for determining its efficacy in inhibiting the binding of $[I^{125}]$-NDP-α-MSH to its receptor. Non-specific binding is measured by complete inhibition of binding of $[I^{125}]$-NDP-α-MSH in the assay with the presence of 1 µM α-MSH.

The assay mixture is incubated for 90 minutes at room temperature, then filtered and the membranes washed three times with ice cold buffer. The filter is dried and counted in a gamma counter for remaining radioactivity bound to the membranes. 100% specific binding is defined as the difference in radioactivity (cpm) bound to cell membranes in the absence and presence of 1 µM α-MSH. The cpm obtained in presence of test metallopeptides are normalized with respect to 100% specific binding to determine the percent inhibition of $[I^{125}]$-NDP-α-MSH binding. Each assay is conducted in triplicate and the actual mean values are described, with results less than 0% reported as 0%.

Competitive binding assay using $[I^{125}]$-AgRP (83-132). Competitive binding studies using $[I^{125}]$-AgRP (83-132) are carried out on membranes isolated from cells expressing hMC4-R. The assay is performed in 96 well GF/B Millipore multiscreen filtration plates (MAFB NOB10) pre-coated with 0.5% bovine serum albumin (Fraction V). The assay mixture contains 25 mM HEPES buffer (pH 7.5) with 100 mM NaCl, 2 mM $CaCl_2$, 2 mM $MgCl_2$, 0.3 mM 1,10-phenanthroline, 0.5% bovine serum albumin, cell membranes, radioligand $[I^{125}]$-AgRP (83-132) (NEN), and increasing concentrations of metallopeptides in a total volume of 200 µL. Binding is measured at radioligand concentrations of 0.2 nM. After incubating for 1 hour at 37° C., the reaction mixture is filtered and washed with an assay buffer containing 500 mM NaCl. The dried discs are punched out from the plate and counted on a gamma counter. Care is taken to limit the specific binding of the ligand to an amount not exceeding 10% of the counts added to the reaction mixture. Data are analyzed using the Prism Graph-Pad curve fitting software.

General method for $EC_{50}$ determination in functional activity assay. Functional evaluation of metallopeptides at melanocortin receptors is performed by measuring the accumulation of intracellular cAMP in HEK-293 cells expressing hMC3-R, hMC4-R or hMC5-R, and in B-16 mouse melanoma cells expressing MC1-R. Cells suspended in Earle's Balanced Salt Solution containing 10 mM HEPES (pH 7.5), 5 mM $MgCl_2$, 1 mM glutamine, 0.1% albumin and 0.6 mM 3-isobutyl-1-methyl-xanthine, a phosphodiesterase inhibitor, are plated in 96 well plates at a density of $0.5 \times 10^5$ cells per well. Cells are incubated with the test metallopeptides in the presence or absence of α-MSH for 1 hour at 37° C. cAMP levels in the cell lysates are measured using an EIA kit (Amersham). Data analysis and $EC_{50}$ values are determined using nonlinear regression analysis with Prism Graph-Pad software.

Functional status. The agonist/antagonist status with respect to MC1-R, MC-3R, MC4-R and MC5-R of certain metallopeptides of the invention is determined. Antagonistic activity is determined by measuring the inhibition of α-MSH-induced or NDP-α-MSH-induced cAMP levels following exposure to graded doses of metallopeptides as in the preceding descriptions.

Assay for agonist. Evaluation of the molecules to elicit a functional response in HEK-293 cells expressing MC4-R for agonistic activity is done by measuring the accumulation of intracellular cAMP following treatment. Confluent HEK-293 cells over-expressing MC4-R are detached by enzyme free cell suspension buffer. Cells are suspended in Earle's Balanced Salt Solution containing 10 mM HEPES (pH 7.5), 1 mM $MgCl_2$, 1 mM glutamine, 0.5% albumin and 0.3 mM 3-isobutyl-1-methyl-xanthine (IBMX), a phosphodiesterase inhibitor. The cells are plated in a 96 well plates at a density of $0.5 \times 10^5$ cells per well and pre-incubated for 30 minutes. The cells are then challenged with the test metallopeptides dissolved in DMSO at a concentration range of 0.05-5000 nM in a total assay volume of 200 µL for 1 hour at 37° C. The concentration of DMSO is always held at 1% in the assay mixture. NDP-α-MSH is used as the reference agonist. At the end of the incubation period the cells are disrupted by the addition of 50 µL of lysis buffer from a cAMP EIA kit (Amersham). Complete rupture of the cells is obtained by pipetting the cells up and down multiple times. cAMP levels in the cell lysates are measured after appropriate dilution using the EIA kit (Amersham) method. Data analysis and $EC_{50}$ values are determined by using nonlinear regression analysis with Prism Graph-Pad software. Metallopeptides at a concentration of 5000 nM that had a response ratio compared to NDP-α-MSH of 0.7 (70%) and above are classified as full agonists. Metallopeptides with a ratio from 0.1 to 0.7 (10% to 70%) are classified as partial agonists. Metallopeptides with a response ratio of less than 0.1 (10%) are optionally evaluated for antagonistic activity.

Assay for Neutral Antagonist. Metallopeptides with a high affinity for binding to MC4-R membranes but with less efficacy ($EC_{50} > 1000$ nM) and low response ratio (<0.1) are analyzed for their ability to antagonize the stimulatory effect of the agonist NDP-α-MSH. These studies are carried out in HEK-293 cells expressing MC4-R. Cells are incubated with the metallopeptides in the presence of the agonist NDP-α-MSH and the extent of antagonism is measured by the decrease in intracellular cAMP concentrations. Screening the metallopeptides for antagonists is done at a single concentration of NDP-α-MSH (1.0 nM) over a metallopeptide concentration range of 0.5-5000 nM. Studies are extended further for metallopeptides exhibiting strong antagonism to derive the $pA_2$ value from Schild's analysis.

Experimental details are similar to the analysis for agonistic activity described above. Briefly, cells are pre-incubated for 30 minutes with the test metallopeptides at concentrations between 0.5 nM and 5000 nM. The cells are then stimulated with NDP-α-MSH at a concentration of 1 nM for 1 hour. For Schild's analysis, the interactions are studied using at least 3 concentrations of the metallopeptides, separated by a log unit, over a full range of the agonist (0.005-5000 nM). cAMP levels are measured in the cell lysates after appropriate dilution. Nonlinear regression analysis with Prism Graph-Pad software was used for Schild's analysis and to obtain $EC_{50}$ values. $pA_2$ values are derived from the Schild's plot of the data.

Assay for inverse agonist. Metallopeptides that had a weak $EC_{50}$ value ($EC_{50} > 1000$ nM) or a low intrinsic activity response ratio (<0.1) are also investigated for their ability to act as inverse agonists, i.e., to decrease the basal or constitutive level of cAMP in HEK-293 cells expressing MC4-R receptors. The experimental protocol is essentially as described above. The cells are exposed to the test metallopeptides over a concentration range of 0.05 nM to 5000 nM for 1 hour at 37° C. AgRP (83-132) is used as the reference inverse agonist. Data analysis and $EC_{50}$ values are determined by using nonlinear regression analysis with the Prism Graph-Pad software.

Penile erection induction. The ability of metallopeptides to induce penile erection (PE) in male rats is evaluated with selected metallopeptides. Male Sprague-Dawley rats weighing 200-250 g are kept on a 12 hour on/off light cycle with food and water ad libitum. All behavioral studies were performed between 10 A.M. and 5 P.M. Groups of 4-8 rats are treated with metallopeptides at a variety of doses via intravenous (IV) or intracerebroventricular (ICV) routes. Immediately after treatment, rats are placed into individual polystyrene cages (27 cm long, 16 cm wide, and 25 cm high) for behavioral observation. Rats are observed for 30 minutes following IV administration or 90 minutes following ICV administration, and the number of yawns, grooming bouts and PEs are recorded in 10-minute bins. Controls utilize carrier without the test metallopeptide. Mean PEs in control groups were 0.17 to 0.5 PEs/rat by IV administration and 0.3 to 0.6 PEs/rat by ICV administration, and thus only PEs with statistically relevant increases over the mean PEs in control groups are reported as inducing PEs.

A PE response in IV animals greater than the mean PEs in control groups but less than 1.0 PEs/rat, particularly with less than all animals responding, are treated as equivocal, and not necessarily distinguishable from vehicle control. In selected instances, metallopeptides with equivocal results in the IV model are tested for penile response in an ICV model, and metallopeptides without a statistically relevant increase over the mean PEs in ICV control groups are determined to not induce PEs.

ICV food intake and body weight change. Change in food intake and body weight is evaluated for selected metallopeptides. Rats with indwelling intracerebroventricular cannulas (ICV rats) are obtained from Hilltop Lab Animals, Inc. (Scottdale, Pa.). Animals are individually housed in conventional plexiglass hanging cages and maintained on a controlled 12 hour on/off light cycle. Water and powdered (LabDiet, 5P00 Prolab RMH 3000) or pelleted (Harlan Teklad 2018 18% Protein Rodent Diet) food is provided ad libitum. For 1 week before treatment, 24-hour food intake and body weight change is recorded to assess a baseline for the group during vehicle treatment. The rats are dosed ICV with vehicle or selected metallopeptides (1-3 nmol). The changes in body weight and food intake for the 24 hour period after dosing are determined. The changes in body weight and food intake for the 48 hour and 72 hour periods after dosing are also measured to determine reversal of changes in body weight and food intake effects back to baseline levels.

IV and IP food intake and body weight change. Change in food intake and body weight is evaluated for selected metallopeptides. Male Sprague-Dawley rats or mice are obtained from Taconic (Germantown, N.Y.). Animals are individually housed in conventional plexiglass hanging cages and maintained on a controlled 12 hour on/off light cycle. Water and powdered (LabDiet, 5P00 Prolab RMH 3000) or pelleted (Harlan Teklad 2018 18% Protein Rodent Diet) food is provided ad libitum. For 1 week before treatment, 24-hour food intake and body weight change is recorded to assess a baseline for the group during vehicle treatment. The rats are dosed IV with vehicle or selected metallopeptides (0.5-3 mg/kg, and in some cases up to 10 mg/Kg) or dosed IP with vehicle or selected metallopeptides (0.5-10 mg/kg, and in some cases up to 50 mg/kg). The changes in body weight and food intake for the 24 hour period after dosing are determined. The changes in body weight and food intake for the 48 hour and 72 hour periods after dosing are also measured to determined reversal of changes in body weight and food intake effects back to baseline levels.

Behavioral Satiety Sequence. Male Sprague-Dawley rats are maintained on a restricted diet of 20 g powdered food per day. Food is presented at the same time during the lights-on period, dosed with either saline or the test metallopeptide 2 hours before presentation of food and the start of observation. Pre-weighed bowls containing 20 g of food are presented and the behavior of the rats was observed for 1 hour. Behavioral observations are divided into 3 categories: Feeding, Active (includes grooming, drinking and sniffing/exploration), and Resting (decreased activity and sleep). The amount of time spent in each behavior is recorded. The amount of food intake is determined after the observation period.

Conditioned Taste Avoidance. Male Sprague-Dawley rats are adapted to a restricted drinking period of 30 minutes per day during lights on and are provided with pelleted chow ad libitum. In laboratory animals the administration of LiCl conditions an aversion to the novel and favorable taste of saccharin (Seeley R J, Blake K, Rushing P A, Benoit S, Eng J, Woods S C and D'Alessio D: The role of CNS glucagons-like peptide-1 (7-36) amide receptors in mediating the visceral illness effects of lithium chloride. *J. Neurosci.* 20(4):1616-1621, 2000). To condition animals, an injection of LiCl or test metallopeptide is administered immediately after the initial presentation of a 0.1% solution of saccharin. Two days later, saccharin solution is again presented and fluid intake is determined. A decrease in drinking the saccharin solution suggests development of a conditioned taste aversion.

Determination of mass and nuclear magnetic resonance analysis. The mass values are determined using a Waters MicroMass ZQ device utilizing a positive mode. Mass determinations are compared with calculated values and expressed in the form of mass weight plus one (M+1 or M+H).

Proton NMR data is obtained using a Bruker 300 MHz spectrometer. The spectra are obtained after dissolving metallopeptides in a deuterated solvent such as chloroform, DMSO, or methanol as appropriate.

The invention is further illustrated by the following non-limiting examples:

EXAMPLE 1

Alpha-MSH with L-Cys Insertion

The first unnumbered peptide (SEQ ID NO:71) in Table 1 is the parent polypeptide, which is an α-MSH analog specific for melanocortin receptors. In particular, it is specific for MC1-R and binds with moderate affinity to MC3-R and MC4-R. It binds very weakly to MC5-R. Peptides were synthesized by conventional solid phase synthetic techniques, complexed with rhenium, separated from solid phase and purified by HPLC. As is well known in the art, Met is not oxidatively stable, and thus during synthesis of these peptides Met was replaced with its oxidatively stable homolog, Nle. Thus SEQ ID NO:1 was used as the template for synthesis of metallopeptides 1-1 through 1-12. The metallopeptides 1-1 through 1-12 have the presumptive metal ion complexation tri-peptide sequence identified in italics. Similarly, the italicized percent inhibition numbers represent metallopeptides wherein the secondary structure of the specific sequence responsible for binding in the parent polypeptide has been presumptively disrupted, as shown by decreased percent inhibition.

The competitive inhibition binding assay was conducted using membranes prepared from hMC3-R, hMC4-R, hMC5-R, and B-16 mouse melanoma cells (containing MC1-R) using 0.4 nM $^{125}$I-NDP-alpha-MSH (New England Nuclear, Boston, Mass., USA) in 50 mM HEPES buffer containing 1 mM $MgCl_2$, 2 mM $CaCl_2$, and 5 mM KCl, at pH 7.2. The assay tube also contained a chosen concentration of the test peptide of this invention complexed to a rhenium metal ion, typically at a 1 µM concentration, for determining its efficacy in inhibiting the binding of $^{125}$I-NDP-α-MSH to its receptor. Non-specific binding was measured by complete inhibition of binding of $^{125}$I-NDP-α-MSH in the assay with the presence of 1 µM α-MSH. Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 µM α-MSH. The cpm obtained in presence of test metallopeptides were normalized with respect to 100% specific binding to determine the percent inhibition of $^{125}$I-NDP-α-MSH binding. Each assay was conducted in triplicate and the actual mean valves are described.

TABLE 1

| No. | Sequence Re-Peptide | % Inhibition at 1 µM at Melanocortin Receptor | | | |
|---|---|---|---|---|---|
| | | 1 | 3 | 4 | 5 |
| Parent | Ac-Ser-Tyr-Ser-Met-Glu-His-Phe-Arg-Trp-Gly-Lys-Pro-Val-$NH_2$ (SEQ ID NO:71)* | 99 | 64 | 69 | 22 |

TABLE 1-continued

| No. | Sequence Re-Peptide | % Inhibition at 1 μM at Melanocortin Receptor | | | |
|---|---|---|---|---|---|
| | | 1 | 3 | 4 | 5 |
| 1-1 | Ac-Ser-Tyr-Ser-Nle-Glu-His-Phe-Arg-Trp-Gly-Lys-*Gly-Val-Cys*-NH₂ (SEQ ID NO:2) | 95 | 48 | 63 | 68 |
| 1-2 | Ac-Ser-Tyr-Ser-Nle-Glu-His-Phe-Arg-Trp-Gly-*Lys-Gly-Cys*-Val-NH₂ (SEQ ID NO:3) | 87 | 6 | 0 | 37 |
| 1-3 | Ac-Ser-Tyr-Ser-Nle-Glu-His-Phe-Arg-Trp-*Gly-Lys-Cys*-Pro-Val-NH₂ (SEQ ID NO:4) | 87 | 0 | 0 | 12 |
| 1-4 | Ac-Ser-Tyr-Ser-Nle-Glu-His-Phe-Arg-*Trp-Gly-Cys*-Lys-Pro-Val-NH₂ (SEQ ID NO:5) | 72 | 0 | 0 | 6 |
| 1-5 | Ac-Ser-Tyr-Ser-Nle-Glu-His-Phe-*Arg-Trp-Cys*-Gly-Lys-Pro-Val-NH₂ (SEQ ID NO:6) | 57 | 0 | 0 | 0 |
| 1-6 | Ac-Ser-Tyr-Ser-Nle-Glu-His-*Phe-Arg-Cys*-Trp-Gly-Lys-Pro-Val-NH₂ (SEQ ID NO:7) | 29 | 0 | 0 | 0 |
| 1-7 | Ac-Ser-Tyr-Ser-Nle-Glu-*His-Phe-Cys*-Arg-Trp-Gly-Lys-Pro-Val-NH₂ (SEQ ID NO:8) | 68 | 0 | 0 | 0 |
| 1-8 | Ac-Ser-Tyr-Ser-Nle-*Glu-His-Cys*-Phe-Arg-Trp-Gly-Lys-Pro-Val-NH₂ (SEQ ID NO:9) | 42 | 0 | 0 | 1 |
| 1-9 | Ac-Ser-Tyr-Ser-*Nle-Glu-Cys*-His-Phe-Arg-Trp-Gly-Lys-Pro-Val-NH₂ (SEQ ID NO:10) | 74 | 0 | 3 | 6 |
| 1-10 | Ac-Ser-Tyr-*Ser-Nle-Cys*-Glu-His-Phe-Arg-Trp-Gly-Lys-Pro-Val-NH₂ (SEQ ID NO:11) | 72 | 0 | 7 | 5 |
| 1-11 | Ac-Ser-*Tyr-Ser-Cys*-Nle-Glu-His-Phe-Arg-Trp-Gly-Lys-Pro-Val-NH₂ (SEQ ID NO:12) | 95 | 18 | 21 | 6 |
| 1-12 | Ac-*Ser-Tyr-Cys*-Ser-Nle-Glu-His-Phe-Arg-Trp-Gly-Lys-Pro-Val-NH₂ (SEQ ID NO:13) | 96 | 15 | 26 | 19 |

*Not complexed to Re metal ion.

EXAMPLE 2

Alpha-MSH with D-Cys Insertion

The first unnumbered peptide in Table 2 is the parent polypeptide, which is the α-MSH analog specific for melanocortin receptors of Example 1. The methods and assays set forth in Example 1 were followed. The metallopeptides 2-1 through 2-12 have the presumptive metal ion complexation tri-peptide sequence identified in italics.

TABLE 2

| No. | Sequence Re-Peptide | % Inhibition at 1 μM at Melanocortin Receptor | | | |
|---|---|---|---|---|---|
| | | 1 | 3 | 4 | 5 |
| Parent | Ac-Ser-Tyr-Ser-Met-Glu-His-Phe-Arg-Trp-Gly-Lys-Pro-Val-NH₂ (SEQ ID NO:71)* | 99 | 64 | 69 | 22 |
| 2-1 | Ac-Ser-Tyr-Ser-Nle-Glu-His-Phe-Arg-Trp-Gly-Lys-*Gly-Val-D-Cys*-NH₂ | 97 | 72 | 46 | 53 |
| 2-2 | Ac-Ser-Tyr-Ser-Nle-Glu-His-Phe-Arg-Trp-Gly-*Lys-Gly-D-Cys*-Val-NH₂ | 93 | 26 | 28 | 32 |
| 2-3 | Ac-Ser-Tyr-Ser-Nle-Glu-His-Phe-Arg-Trp-*Gly-Lys-D-Cys*-Pro-Val-NH₂ | 91 | 41 | 25 | 38 |
| 2-4 | Ac-Ser-Tyr-Ser-Nle-Glu-His-Phe-Arg-*Trp-Gly-D-Cys*-Lys-Pro-Val-NH₂ | 91 | 27 | 40 | 21 |
| 2-5 | Ac-Ser-Tyr-Ser-Nle-Glu-His-Phe-*Arg-Trp-D-Cys*-Gly-Lys-Pro-Val-NH₂ | 43 | 0 | 4 | 0 |
| 2-6 | Ac-Ser-Tyr-Ser-Nle-Glu-His-*Phe-Arg-D-Cys*-Trp-Gly-Lys-Pro-Val-NH₂ | 46 | 2 | 6 | 6 |
| 2-7 | Ac-Ser-Tyr-Ser-Nle-Glu-*His-Phe-D-Cys*-Arg-Trp-Gly-Lys-Pro-Val-NH₂ | 54 | 0 | 6 | 0 |
| 2-8 | Ac-Ser-Tyr-Ser-Nle-*Glu-His-D-Cys*-Phe-Arg-Trp-Gly-Lys-Pro-Val-NH₂ | 69 | 0 | 25 | 29 |
| 2-9 | Ac-Ser-Tyr-Ser-*Nle-Glu-D-Cys*-His-Phe-Arg-Trp-Gly-Lys-Pro-Val-NH₂ | 92 | 13 | 35 | 2 |
| 2-10 | Ac-Ser-Tyr-*Ser-Nle-D-Cys*-Glu-His-Phe-Arg-Trp-Gly-Lys-Pro-Val-NH₂ | 65 | 0 | 18 | 0 |
| 2-11 | Ac-Ser-*Tyr-Ser-D-Cys*-Nle-Glu-His-Phe-Arg-Trp-Gly-Lys-Pro-Val-NH₂ | 95 | 5 | 37 | 0 |
| 2-12 | Ac-*Ser-Tyr-D-Cys*-Ser-Nle-Glu-His-Phe-Arg-Trp-Gly-Lys-Pro-Val-NH₂ | 97 | 21 | 47 | 17 |

*Not complexed to Re metal ion.

As in Example 1, the parent molecule is a specific ligand for MC1-R and exhibits moderate to low binding to MC3-R, MC4-R, and MC5-R.

EXAMPLE 3

[Nle³, D-Phe⁶]-Gamma-MSH L-Cys Insertion

The first unnumbered peptide in Table 3 is the parent polypeptide, which is a Nle³, D-Phe⁶ substituted γ-MSH analog specific for melanocortin receptors. The methods and assays set forth in Example 1 were followed. The metallopeptides have the presumptive metal ion complexation tri-peptide sequence identified in italics, with L-Cys inserted.

TABLE 3

| No. | Sequence Re-Peptide | % Inhibition at 1 μM at Melanocortin Receptor | | | |
|---|---|---|---|---|---|
| | | 1 | 3 | 4 | 5 |
| Parent | Tyr-Val-Nle-Gly-His-D-phe-Arg-Trp-Asp-Arg-Phe-NH₂* | 99 | 100 | 99 | 100 |
| 3-1 | Tyr-Val-Nle-Gly-His-D-Phe-Arg-Trp-Asp-*Arg-Phe-Cys*-NH₂ | 95 | 96 | 98 | 102 |
| 3-2 | Tyr-Val-Nle-Gly-His-D-Phe-Arg-Trp-*Asp-Arg-Cys*-Phe-NH₂ | 99 | 91 | 89 | 100 |
| 3-3 | Tyr-Val-Nle-Gly-His-D-Phe-Arg-*Trp-Asp-Cys*-Arg-Phe-NH₂ | 99 | 95 | 99 | 99 |
| 3-4 | Tyr-Val-Nle-Gly-His-D-Phe-*Arg-Trp-Cys*-Asp-Arg-Phe-NH₂ | 98 | 88 | 94 | 100 |
| 3-5 | Tyr-Val-Nle-Gly-His-D-*Phe-Arg-Cys*-Trp-Asp-Arg-Phe-NH₂ | 83 | 45 | 33 | 81 |
| 3-6 | Tyr-Val-Nle-Gly-*His-D-Phe-Cys*-Arg-Trp-Asp-Arg-Phe-NH₂ | 52 | 20 | 31 | 31 |
| 3-7 | Tyr-Val-Nle-*Gly-His-Cys*-D-Phe-Arg-Trp-Asp-Arg-Phe-NH₂ | 39 | 50 | 28 | 56 |
| 3-8 | Tyr-Val-Nle-*Gly-His-Cys*-D-Phe-Arg-Trp-Asp-Arg-Phe-NH₂ | 86 | 60 | 55 | 84 |
| 3-9 | Tyr-Val-*Nle-Gly-Cys*-His-D-Phe-Arg-Trp-Asp-Arg-Phe-NH₂ | 77 | 69 | 55 | 67 |
| 3-10 | Tyr-*Val-Nle-Cys*-Gly-His-D-Phe-Arg-Trp-Asp-Arg-Phe-NH₂ | 84 | 78 | 80 | 86 |
| 3-11 | *Tyr-Val-Cys*-Nle-Gly-His-D-Phe-Arg-Trp-Asp-Arg-Phe-NH₂ | 95 | 85 | 82 | 92 |

*Not complexed to Re metal ion.

The parent peptide binds to MC1-R, MC3-R, MC4-R, and MC5-R with high affinity.

EXAMPLE 4

[Nle³]-Gamma-MSH L-Cys Insertion

The first unnumbered peptide in Table 4 is the parent polypeptide, which is a Nle³ substituted γ-MSH analog specific for melanocortin receptors. The methods and assays set forth in Example 1 were followed. The metallopeptides have the presumptive metal ion complexation tri-peptide sequence identified in italics, with L-Cys inserted.

TABLE 4

| No. | Sequence | % Inhibition at 1 μM at Melanocortin Receptor | | | |
|---|---|---|---|---|---|
| | | 1 | 3 | 4 | 5 |
| Parent | Tyr-Val-Nle-Gly-His-Phe-Arg-Trp-Asp-Arg-Phe-NH₂ (SEQ ID NO:14)* | 83 | 85 | 58 | 43 |
| 4-1 | Tyr-Val-Nle-Gly-His-Phe-Arg-Trp-Asp-*Arg-Phe-Cys*-NH₂ (SEQ ID NO:15) | 56 | 69 | 36 | 41 |
| 4-2 | Tyr-Val-Nle-Gly-His-Phe-Arg-Trp-*Asp-Arg-Cys*-Phe-NH₂ (SEQ ID NO:16) | 75 | 49 | 23 | 51 |
| 4-3 | Tyr-Val-Nle-Gly-His-Phe-Arg-*Trp-Asp-Cys*-Arg-Phe-NH₂ (SEQ ID NO:17) | 44 | 18 | 23 | 65 |
| 4-4 | Tyr-Val-Nle-Gly-His-Phe-*Arg-Trp-Cys*-Asp-Arg-Phe-NH₂ (SEQ ID NO:18) | 52 | 20 | 39 | 47 |
| 4-5 | Tyr-Val-Nle-Gly-His-*Phe-Arg-Cys*-Trp-Asp-Arg-Phe-NH₂ (SEQ ID NO:19) | 89 | 87 | 74 | 68 |
| 4-6 | Tyr-Val-Nle-Gly-*His-Phe-Cys*-Arg-Trp-Asp-Arg-Phe-NH₂ (SEQ ID NO:20) | -8 | 5 | -2 | 24 |
| 4-7 | Tyr-Val-Nle-*Gly-His-Cys*-Phe-Arg-Trp-Asp-Arg-Phe-NH₂ (SEQ ID NO:21) | -4 | 17 | 4 | 15 |
| 4-8 | Tyr-Val-*Nle-Gly-Cys*-His-Phe-Arg-Trp-Asp-Arg-Phe-NH₂ (SEQ ID NO:22) | 13 | 33 | -1 | 45 |
| 4-9 | Tyr-*Val-Nle-Cys*-Gly-His-Phe-Arg-Trp-Asp-Arg-Phe-NH₂ (SEQ ID NO:23) | 1 | 19 | 4 | 43 |
| 4-10 | *Tyr-Val-Cys*-Nle-Gly-His-Phe-Arg-Trp-Asp-Arg-Phe-NH₂ (SEQ ID NO:24) | 28 | 10 | 2 | 17 |

*Not complexed to Re metal ion.

[Nle³]-γ-MSH is not as potent a ligand for various melanocortin receptors as [Nle³, D-Phe⁶]-γ-MSH described in Example 3. It has high affinity for MC1-R and MC3-R and moderate affinity for MC4-R and MC5-R. As is shown from the data presented in Table 4, metallopeptide 4-5 with a Phe-Arg-Cys metal complexation sequence preserved all receptor binding of the parent polypeptide. This metallopeptide therefore positively demonstrates that the bioactive structure around the His-Phe-Arg-Trp (SEQ ID NO:63) messenger sequence is stabilized for all the receptors by metal ion complexation.

EXAMPLE 5

[Nle$^3$, D-Phe$^6$]-Gamma-MSH L-Cys Substitution

The first unnumbered peptide in Table 5 is the parent polypeptide, which is a γ-MSH analog specific for melanocortin receptors. The methods and assays set forth in Example 1 were followed. The metallopeptides have the presumptive metal ion complexation tri-peptide sequence identified in italics with L-Cys insertion.

TABLE 5

| No. | Sequence Re-Peptide | % Inhibition at 1 μM at Melanocortin Receptor | | | |
|---|---|---|---|---|---|
| | | 1 | 3 | 4 | 5 |
| Parent | Tyr-Val-Nle-Gly-His-D-Phe-Arg-Trp-Asp-Arg-Phe-NH$_2$* | 99 | 100 | 99 | 100 |
| 5-1 | Tyr-Val-Nle-Gly-His-D-Phe-Arg-Trp-*Asp-Arg-Cys*-NH$_2$ | 101 | 92 | 95 | 98 |
| 5-2 | Tyr-Val-Nle-Gly-His-D-Phe-Arg-*Trp-Asp-Cys*-Phe-NH$_2$ | 95 | 39 | 58 | 61 |
| 5-3 | Tyr-Val-Nle-Gly-His-D-Phe-*Arg-Trp-Cys*-Arg-Phe-NH$_2$ | 100 | 93 | 97 | 100 |
| 5-4 | Tyr-Val-Nle-Gly-His-*D-Phe-Arg-Cys*-Asp-Arg-Phe-NH$_2$ | 86 | 11 | 18 | 58 |
| 5-5 | Tyr-Val-Nle-Gly-*His-D-Phe-Cys*-Trp-Asp-Arg-Phe-NH$_2$ | 67 | 15 | 26 | 28 |
| 5-6 | Tyr-Val-Nle-*Gly-His-Cys*-Arg-Trp-Asp-Arg-Phe-NH$_2$ (SEQ ID NO:64) | 74 | 26 | 4 | 21 |
| 5-7 | Tyr-Val-*Nle-Gly-Cys*-D-Phe-Arg-Trp-Asp-Arg-Phe-NH$_2$ | 89 | 70 | 69 | 88 |
| 5-8 | Tyr-*Val-Nle-Cys*-His-D-Phe-Arg-Trp-Asp-Arg-Phe-NH$_2$ | 95 | 89 | 86 | 98 |
| 5-9 | *Tyr-Val-Cys*-Gly-His-D-Phe-Arg-Trp-Asp-Arg-Phe-NH$_2$ | 89 | 53 | 66 | 53 |

*Not complexed to Re metal ion.

The parent peptide binds to MC1-R, MC3-R, MC4-R and MC5-R with high affinity

EXAMPLE 6

Bombesin with L-Cys Insertion

Here and in the following examples bombesin or bombesin-like peptides were employed. The function of bombesin peptides, and potential parent polypeptides, are disclosed in the scientific literature, including Leban J J et al: *Proc Natl Acad Sci USA* 90:1922-1925, 1993; Hampton L L et al: *Proc Natl Acad Sci USA* 95:3188-3192, 1998; and Yamada K, Wada E and Wada K: *Ann Med* 32:519-529, 2000, all incorporated here by reference. The peptide Pyr-Gln-Arg-Leu-Gly-Asn-Gln-Trp-Ala-Val-Gly-His-Leu-Met-NH$_2$ (SEQ ID NO:72) was employed as the control, with the template based on SEQ ID NO:25 wherein Nle$^{14}$ was substituted for Met$^{14}$ as in Example 1.

Rat brain membranes were utilized as the source of bombesin receptor. The competitive binding assay was performed using a procedure as described by Moody T W, Perk C B, Rivier J, Brown, M R. (*Proc Natl Acad Sci USA.* 75:5372-5376, 1985) and adapted to a 96 well format. An aliquot of membranes taken in assay buffer (50 mM Tris and HCl, pH 7.4 containing 1 mg/mL BSA and 2 μg/mL bacitracin) was incubated with 0.01 nM of $^{125}$I-Bombesin with or without varying concentrations of the test metallopeptide for 60 min at 4° C. The incubation was terminated by rapid filtration of the assay mixture, followed by washing the filters with ice-cold buffer. The filters were dried and counted in a gamma counter for retained radioactivity. Non-specific binding was measured by including 1 μM bombesin in the assay tube. The assay was performed in triplicate and results calculated to determine percentage inhibition of the $^{125}$I-Bombesin binding to its receptors by a test metallopeptide. The parent polypeptide is shown in Table 6, with metallopeptides having Cys inserted as shown.

TABLE 6

| No. | Sequence Re-Peptide | % Inhibition |
|---|---|---|
| Parent | Pyr-Gln-Arg-Leu-Gly-Asn-Gln-Trp-Ala-Val-Gly-His-Leu-Met-NH$_2$ (SEQ ID NO:72)* | 106 |
| 6-1 | Pyr-Gln-Arg-Leu-Gly-Asn-Gln-Trp-Ala-Val-Gly-His-*Leu-Nle-Cys*-NH$_2$ (SEQ ID NO:26) | 82 |
| 6-2 | Pyr-Gln-Arg-Leu-Gly-Asn-Gln-Trp-Ala-Val-Gly-*His-Leu-Cys*-Nle-NH$_2$ (SEQ ID NO:27) | 91 |
| 6-3 | Pyr-Gln-Arg-Leu-Gly-Asn-Gln-Trp-Ala-Val-*Gly-His-Cys*-Leu-Nle-NH$_2$ (SEQ ID NO:28) | 71 |
| 6-4 | Pyr-Gln-Arg-Leu-Gly-Asn-Gln-Trp-Ala-*Val-Gly-Cys*-His-Leu-Nle-NH$_2$ (SEQ ID NO:29) | 70 |
| 6-5 | Pyr-Gln-Arg-Leu-Gly-Asn-Gln-Trp-Ala-*Val-Cys*-Gly-His-Leu-Nle-NH$_2$ (SEQ ID NO:30) | 67 |
| 6-6 | Pyr-Gln-Arg-Leu-Gly-Asn-Gln-*Trp-Ala-Cys*-Val-Gly-His-Leu-Nle-NH$_2$ (SEQ ID NO:31) | 83 |
| 6-7 | Pyr-Gln-Arg-Leu-Gly-Asn-*Gln-Trp-Cys*-Ala-Val-Gly-His-Leu-Nle-NH$_2$ (SEQ ID NO:32) | 62 |

TABLE 6-continued

| No. | Sequence Re-Peptide | % Inhibition |
|---|---|---|
| 6-8 | Pyr-Gln-Arg-Leu-Gly-*Asn-Gln-Cys*-Trp-Ala-Val-Gly-His-Leu-Nle-NH$_2$ (SEQ ID NO:33) | 75 |
| 6-9 | Pyr-Gln-Arg-Leu-*Gly-Asn-Cys*-Gln-Trp-Ala-Val-Gly-His-Leu-Nle-NH$_2$ (SEQ ID NO:34) | 91 |
| 6-10 | Pyr-Gln-Arg-*Leu-Gly-Cys*-Asn-Gln-Trp-Ala-Val-Gly-His-Leu-Nle-NH$_2$ (SEQ ID NO:35) | 93 |
| 6-11 | Pyr-Gln-*Arg-Leu-Cys*-Gly-Asn-Gln-Trp-Ala-Val-Gly-His-Leu-Nle-NH$_2$ (SEQ ID NO:36) | N.D. |
| 6-12 | Pyr-*Gln-Arg-Cys*-Leu-Gly-Asn-Gln-Trp-Ala-Val-Gly-His-Leu-Nle-NH$_2$ (SEQ ID NO:37) | 97 |
| 6-13 | Ac-*Ala-Gln-Cys*-Arg-Leu-Gly-Asn-Gln-Trp-Ala-Val-Gly-His-Leu-Nle-NH$_2$ (SEQ ID NO:38) | 99 |

(N.D. indicates "not determined.")
*Not complexed to Re metal ion.

The parent peptide is a natural bombesin molecule isolated from amphibian skin (Anastasi A et al: *Experinetia* 27:166-167, 1971) wherein Met has been replaced with Nle.

EXAMPLE 7

Bombesin With L-Cys Substitution

Using the parent polypeptide and methods of Example 6, a second series of metallopeptides were constructed and tested using L-Cys substitution, as shown in Table 7.

TABLE 7

| No. | Sequence Re-Peptide | % Inhibition |
|---|---|---|
| Parent | Pyr-Gln-Arg-Leu-Gly-Asn-Gln-Trp-Ala-Val-Gly-His-Leu-Met-NH$_2$ (SEQ ID NO:72)* | 106 |
| 7-1 | Pyr-Gln-Arg-Leu-Gly-Asn-Gln-Trp-Ala-Val-Gly-*His-Leu-Cys*-NH$_2$ (SEQ ID NO:40) | 73 |
| 7-2 | Pyr-Gln-Arg-Leu-Gly-Asn-Gln-Trp-Ala-Val-*Gly-His-Cys*-Nle-NH$_2$ (SEQ ID NO:41) | 66 |
| 7-3 | Pyr-Gln-Arg-Leu-Gly-Asn-Gln-Trp-Ala-*Val-Gly-Cys*-Leu-Nle-NH$_2$ (SEQ ID NO:42) | 82 |
| 7-4 | Pyr-Gln-Arg-Leu-Gly-Asn-Gln-Trp-*Ala-Val-Cys*-His-Leu-Nle-NH$_2$ (SEQ ID NO:43) | 81 |
| 7-5 | Pyr-Gln-Arg-Leu-Gly-Asn-Gln-Trp-*Ala-Cys*-Gly-His-Leu-Nle-NH$_2$ (SEQ ID NO:44) | 61 |
| 7-6 | Pyr-Gln-Arg-Leu-Gly-Asn-*Gln-Trp-Cys*-Val-Gly-His-Leu-Nle-NH$_2$ (SEQ ID NO:45) | 91 |

TABLE 7-continued

| No. | Sequence Re-Peptide | % Inhibition |
|---|---|---|
| 7-7 | Pyr-Gln-Arg-Leu-Gly-*Asn-Gln-Cys*-Ala-Val-Gly-His-Leu-Nle-NH$_2$ (SEQ ID NO:46) | -2 |
| 7-8 | Pyr-Gln-Arg-Leu-*Gly-Asn-Cys*-Trp-Ala-Val-Gly-His-Leu-Nle-NH$_2$ (SEQ ID NO:47) | 84 |
| 7-9 | Pyr-Gln-Arg-*Leu-Gly-Cys*-Gln-Trp-Ala-Val-Gly-His-Leu-Nle-NH$_2$ (SEQ ID NO:48) | 93 |
| 7-10 | Pyr-Gln-*Arg-Leu-Cys*-Asn-Gln-Trp-Ala-Val-Gly-His-Leu-Nle-NH$_2$ (SEQ ID NO:49) | N.D. |
| 7-11 | Pyr-*Gln-Arg-Cys*-Gly-Asn-Gln-Trp-Ala-Val-Gly-His-Leu-Nle-NH$_2$ (SEQ ID NO:50) | 95 |
| 7-12 | Ac-*Ala-Gln-Cys*-Leu-Gly-Asn-Gln-Trp-Ala-Val-Gly-His-Leu-Nle-NH$_2$ (SEQ ID NO:51) | 96 |

(N.D. indicates "not determined.")
*Not complexed to Re metal ion.

EXAMPLE 8

Alternative Bombesin with L-Cys Insertion

Using the competitive inhibition methods of Example 6, the parent polypeptide of Table 8 was used to construct the L-Cys insertion metallopeptides shown.

TABLE 8

| No. | Sequence Re-Peptide | % Inhibition |
|---|---|---|
| Parent | D-Phe-Gln-Trp-Ala-Val-Gly-His-Leu-Leu-NH$_2$* | 92 |
| 8-1 | D-Phe-Gln-Trp-Ala-Val-Gly-His-Leu-Leu-Cys-NH$_2$ | 39 |
| 8-2 | D-Phe-Gln-Trp-Ala-Val-Gly-*His-Leu-Cys*-Leu-NH$_2$ | 75 |
| 8-3 | D-Phe-Gln-Trp-Ala-Val-*Gly-His-Cys*-Leu-Leu-NH$_2$ | 49 |
| 8-4 | D-Phe-Gln-Trp-Ala-*Val-Gly-Cys*-His-Leu-Leu-NH$_2$ | 59 |
| 8-5 | D-Phe-Gln-Trp-*Ala-Val-Cys*-Gly-His-Leu-Leu-NH$_2$ | 70 |
| 8-6 | D-Phe-Gln-*Trp-Ala-Cys*-Val-Gly-His-Leu-Leu-NH$_2$ | 35 |
| 8-7 | D-Phe-Gln-*Trp-Cys*-Ala-Val-Gly-His-Leu-Leu-NH$_2$ | 8 |
| 8-8 | D-*Phe-Gln-Cys*-Trp-Ala-Val-Gly-His-Leu-Leu-NH$_2$ | 62 |

*Not complexed to Re metal ion.

The parent polypeptide is a potent nine amino acid peptide analog of bombesin (Deschodt-Lanckman M. et al: In vitro actions of bombesin-like peptides in amylase secretion, calcium efflux and adenyl cyclase activity in rat pancreas. *J Clin Invest* 58; 891-898, 1976).

EXAMPLE 9

Alternative Bombesin with L-Cys Substitution

An L-Cys substitution scheme was employed, using the parent polypeptide disclosed in Example 8 and the competitive inhibition methods of Example 6.

TABLE 9

| No. | Sequence Re-Peptide | % Inhibition |
|---|---|---|
| Parent | D-Phe-Gln-Trp-Ala-Val-Gly-His-Leu-Leu-NH$_2$* | 92 |
| 9-1 | D-Phe-Gln-Trp-Ala-Val-Gly-*His-Leu-Cys*-NH$_2$ | 86 |
| 9-2 | D-Phe-Gln-Trp-Ala-Val-*Gly-His-Cys*-Leu-NH$_2$ | 35 |
| 9-3 | D-Phe-Gln-Trp-Ala-*Val-Gly-Cys*-Leu-Leu-NH$_2$ | 70 |
| 9-4 | D-Phe-Gln-Trp-*Ala-Val-Cys*-His-Leu-Leu-NH$_2$ | 75 |
| 9-5 | D-Phe-Gln-*Trp-Ala-Cys*-Gly-His-Leu-Leu-NH$_2$ | 17 |
| 9-6 | D-Phe-*Gln-Trp-Cys*-Val-Gly-His-Leu-Leu-NH$_2$ | 43 |
| 9-7 | D-*Phe-Gln-Cys*-Ala-Val-Gly-His-Leu-Leu-NH$_2$ | 19 |

*Not complexed to Re metal ion.

EXAMPLE 10

Further Bombesin Evaluation

Based on the metallopeptide 9-4 disclosed in Table 9, and using the methods of Example 6, a series of metallopeptides was constructed by modifying the Cys and its flanking residues sequentially with D-variants as shown.

TABLE 10

| No. | Sequence Re-Peptide | % Inhibition |
|---|---|---|
| 9-4 | D-Phe-Gln-Trp-*Ala-Val-Cys*-His-Leu-Leu-NH$_2$ | 75 |
| 10-1 | D-Phe-Gln-Trp-*Ala-Val-Cys*-D-His-Leu-Leu-NH$_2$ | 10 |
| 10-2 | D-Phe-Gln-Trp-*Ala-Val-Cys*-His-Leu-Leu-NH$_2$ | 64 |
| 10-3 | D-Phe-Gln-Trp-*Ala-D-Val-Cys*-His-Leu-Leu-NH$_2$ | 7 |
| 10-4 | D-Phe-Gln-Trp-*D-Ala-Val-Cys*-His-Leu-Leu-NH$_2$ | 2 |
| 10-5 | D-Phe-Gln-D-Trp-*Ala-Val-Cys*-His-Leu-Leu-NH$_2$ | 6 |

EXAMPLE 11

Further Bombesin Evaluation

Using the 9-4 metallopeptide of Table 9, and the methods of Example 6, a series of metallopeptides was constructed modifying the length of metallopeptide 9-4, with truncation at either or both the C- and N-terminus, as shown in Table 11.

TABLE 11

| No. | Sequence Re-Peptide | | % Inhibition |
|---|---|---|---|
| 9-4 | D-Phe-Gln-Trp-*Ala-Val-Cys*-His-Leu-Leu-NH$_2$ | | 75 |
| 11-1 | D-Phe-Gln-Trp-*Ala-Val-Cys*-His-Leu-NH$_2$ | | 98 |
| 11-2 | D-Phe-Gln-Trp-*Ala-Val-Cys*-His-NH$_2$ | | 25 |
| 11-3 | D-Phe-Gln-Trp-*Ala-Val-Cys*-NH$_2$ | | -81 |
| 11-4 | Gln-Trp-*Ala-Val-Cys*-His-Leu-Leu-NH$_2$ | (SEQ ID NO:52) | 25 |
| 11-5 | Trp-*Ala-Val-Cys*-His-Leu-Leu-NH$_2$ | (SEQ ID NO:53) | 18 |
| 11-6 | *Ala-Val-Cys*-His-Leu-Leu-NH$_2$ | (SEQ ID NO:54) | 6 |
| 11-7 | Gln-Trp-*Ala-Val-Cys*-His-Leu-NH$_2$ | (SEQ ID NO:55) | 5 |
| 11-8 | Trp-*Ala-Val-Cys*-His-Leu-NH$_2$ | (SEQ ID NO:56) | 13 |
| 11-9 | *Ala-Val-Cys*-His-Leu-NH$_2$ | (SEQ ID NO:57) | 7 |
| 11-10 | Gln-Trp-*Ala-Val-Cys*-His-NH$_2$ | (SEQ ID NO:58) | N.D. |
| 11-11 | Trp-*Ala-Val-Cys*-His-NH$_2$ | (SEQ ID NO:59) | -1 |
| 11-12 | *Ala-Val-Cys*-His-NH$_2$ | (SEQ ID NO:60) | 5 |
| 11-13 | Gln-Trp-*Ala-Val-Cys*-NH$_2$ | (SEQ ID NO:61) | -50 |

TABLE 11-continued

| No. | Sequence Re-Peptide | | % Inhibition |
|---|---|---|---|
| 11-14 | Trp-*Ala-Val-Cys*-NH$_2$ | (SEQ ID NO:62) | 8 |
| 11-15 | *Ala-Val-Cys*-NH$_2$ | | 4 |

(N.D. indicates "not determined.")

The results presented in Table 11 show that truncation of the terminal Leu at the C-terminus of metallopeptide 9-4 enhanced potency.

EXAMPLE 12

Further Bombesin Evaluation

Again using the metallopeptide 9-4 of Table 9, and the methods of Example 6, a series of metallopeptides were constructed with amino-acid residue substitution and deletion as shown in Table 12.

TABLE 12

| No. | Sequence Re-Peptide | % Inhibition |
|---|---|---|
| 9-4 | D-Phe-Gln-Trp-*Ala-Val-Cys*-His-Leu-Leu-NH$_2$ | 75 |
| 12-1 | D-Phe-Gln-*Trp-Val-Cys*-Gly-His-Leu-Leu-NH$_2$ | 2 |
| 12-2 | D-Phe-Gln-*Trp-Ala-Cys*-Val-His-Leu-Leu-NH$_2$ | 3 |
| 12-3 | D-Phe-Gln-*Trp-Val-Cys*-Val-His-Leu-Leu-NH$_2$ | 14 |
| 12-4 | D-Phe-Gln-*Trp-Val-Cys*-His-Leu-Leu-NH$_2$ | 5 |
| 12-5 | D-Phe-*Gln-Trp-Cys*-Val-Gly-His-Leu-Leu-NH$_2$ | 43 |
| 12-6 | D-Phe-*Gln-Trp-Cys*-Val-His-Leu-Leu-NH$_2$ | 10 |

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A metallopeptide comprising a biologically active alpha-melanocyte stimulating hormone (α-MSH) sequence selected from the group consisting of Ac-Ser-Tyr-Ser-Nle-Glu-His-Phe-Arg-Trp-Gly-Lys-Pro-Val-NH$_2$ (SEQ ID NO:1) and Ac-Ser-Tyr-Ser-Met-Glu-His-Phe-Arg-Trp-Gly-Lys-Pro-Val-NH$_2$ (SEQ ID NO:71), wherein an amino acid residue comprising a nitrogen atom and sulfur atom each available for complexation to a metal ion is inserted at any position from between the two and three position to the C-terminus position, with a rhenium or technetium metal ion complexed thereto to form an N$_3$S$_1$ ligand, wherein any proline (Pro) residue which is either of the two residues on the immediately adjacent N-terminus side of the inserted residue comprising a nitrogen atom and sulfur atom available for complexation to a metal ion is substituted with Gly, Ala, Ser, Aib, 1-amino, 1-cyclopentane carboxylic acid or ΔAla.

2. The metallopeptide of claim 1 wherein the metal ion is rhenium.

3. The metallopeptide of claim 1 wherein the α-MSH sequence is Ac-Ser-Tyr-Ser-Nle-Glu-His-Phe-Arg-Trp-Gly-Lys-Pro-Val-NH$_2$ (SEQ ID NO:1).

4. The metallopeptide of claim 3 wherein the residue comprising a nitrogen and sulfur atom is L-Cys and the metallopeptide sequence is selected from the group consisting of:

```
Ac-Ser-Tyr-Ser-Nle-Glu-His-Phe-Arg-Trp-Gly-Lys-Gly-Val-Cys-NH₂,    (SEQ ID NO:2)

Ac-Ser-Tyr-Ser-Nle-Glu-His-Phe-Arg-Trp-Gly-Lys-Gly-Cys-Val-NH₂,    (SEQ ID NO:3)

Ac-Ser-Tyr-Ser-Nle-Glu-His-Phe-Arg-Trp-Gly-Lys-Cys-Pro-Val-NH₂,    (SEQ ID NO:4)

Ac-Ser-Tyr-Ser-Nle-Glu-His-Phe-Arg-Trp-Gly-Cys-Lys-Pro-Val-NH₂,    (SEQ ID NO:5)

Ac-Ser-Tyr-Ser-Nle-Glu-His-Phe-Arg-Trp-Cys-Gly-Lys-Pro-Val-NH₂,    (SEQ ID NO:6)

Ac-Ser-Tyr-Ser-Nle-Glu-His-Phe-Arg-Cys-Trp-Gly-Lys-Pro-Val-NH₂,    (SEQ ID NO:7)

Ac-Ser-Tyr-Ser-Nle-Glu-His-Phe-Cys-Arg-Trp-Gly-Lys-Pro-Val-NH₂,    (SEQ ID NO:8)

Ac-Ser-Tyr-Ser-Nle-Glu-His-Cys-Phe-Arg-Trp-Gly-Lys-Pro-Val-NH₂,    (SEQ ID NO:9)

Ac-Ser-Tyr-Ser-Nle-Glu-Cys-His-Phe-Arg-Trp-Gly-Lys-Pro-Val-NH₂,    (SEQ ID NO:10)

Ac-Ser-Tyr-Ser-Nle-Cys-Glu-His-Phe-Arg-Trp-Gly-Lys-Pro-Val-NH₂,    (SEQ ID NO:11)

Ac-Ser-Tyr-Ser-Cys-Nle-Glu-His-Phe-Arg-Trp-Gly-Lys-Pro-Val-NH₂,    (SEQ ID NO:12)
or

Ac-Ser-Tyr-Cys-Ser-Nle-Glu-His-Phe-Arg-Trp-Gly-Lys-Pro-Val-NH₂.    (SEQ ID NO:13)
```

5. The metallopeptide of claim 3 wherein the residue comprising a nitrogen and sulfur atom is D-Cys and the metallopeptide sequence is selected from the group consisting of:

```
Ac-Ser-Tyr-Ser-Nle-Glu-His-Phe-Arg-Trp-Gly-Lys-Gly-Val-D-Cys-NH₂,

Ac-Ser-Tyr-Ser-Nle-Glu-His-Phe-Arg-Trp-Gly-Lys-Gly-D-Cys-Val-NH₂,

Ac-Ser-Tyr-Ser-Nle-Glu-His-Phe-Arg-Trp-Gly-Lys-D-Cys-Pro-Val-NH₂,

Ac-Ser-Tyr-Ser-Nle-Glu-His-Phe-Arg-Trp-Gly-D-Cys-Lys-Pro-Val-NH₂,

Ac-Ser-Tyr-Ser-Nle-Glu-His-Phe-Arg-Trp-D-Cys-Gly-Lys-Pro-Val-NH₂,

Ac-Ser-Tyr-Ser-Nle-Glu-His-Phe-Arg-D-Cys-Trp-Gly-Lys-Pro-Val-NH₂,

Ac-Ser-Tyr-Ser-Nle-Glu-His-Phe-D-Cys-Arg-Trp-Gly-Lys-Pro-Val-NH₂,

Ac-Ser-Tyr-Ser-Nle-Glu-His-D-Cys-Phe-Arg-Trp-Gly-Lys-Pro-Val-NH₂,

Ac-Ser-Tyr-Ser-Nle-Glu-D-Cys-His-Phe-Arg-Trp-Gly-Lys-Pro-Val-NH₂,

Ac-Ser-Tyr-Ser-Nle-D-Cys-Glu-His-Phe-Arg-Trp-Gly-Lys-Pro-Val-NH₂,

Ac-Ser-Tyr-Ser-D-Cys-Nle-Glu-His-Phe-Arg-Trp-Gly-Lys-Pro-Val-NH₂,
or

Ac-Ser-Tyr-D-Cys-Ser-Nle-Glu-His-Phe-Arg-Trp-Gly-Lys-Pro-Val-NH₂.
```

6. A metallopeptide comprising a biologically active α-MSH sequence selected from the group consisting of Ac-Ser-Tyr-Ser-Nle-Glu-His-Phe-Arg-Trp-Gly-Lys-Pro-Val-NH$_2$ (SEQ ID NO:1) and Ac-Ser-Tyr-Ser-Met-Glu-His-Phe-Arg-Trp-Gly-Lys-Pro-Val-NH$_2$ (SEQ ID NO:71), wherein a an amino acid residue comprising a nitrogen atom and sulfur atom each available for complexation to a metal ion is substituted for the residue at any position from the three position to the C-terminus position, with a rhenium or technetium metal ion complexed thereto to form an N$_3$S$_1$ ligand, wherein any Pro residue which is either of the two residues on the immediately adjacent N-terminus side of the substituent residue comprising a nitrogen atom and sulfur atom available for complexation to a metal ion is substituted with Gly, Ala, Ser, Aib, 1-amino, 1-cyclopentane carboxylic acid or ΔAla.

7. The metallopeptide of claim 6 wherein the metal ion is rhenium.

8. A metallopeptide comprising a biologically active alpha-melanocyte stimulating hormone (α-MSH) selected from the group consisting of Ac-Ser-Tyr-Ser-Nle-Glu-His-Phe-Arg-Trp-Gly-Lys-Pro-Val-NH$_2$ (SEQ ID NO:1) and Ac-Ser-Tyr-Ser-Met-Glu-His-Phe-Arg-Trp-Gly-Lys-Pro-Val-NH$_2$ (SEQ ID NO:71), wherein a an amino acid residue comprising a nitrogen atom and sulfur atom each available for complexation to a metal ion is either (a) inserted at any position from between the two and three position to the C-terminus position, or (b) substituted for the residue at any position from the three position to the C-terminus position, in either instance with a rhenium or technetium metal ion complexed thereto to form an N$_3$S$_1$ ligand, wherein any proline (Pro) residue which is either of the two residues on the immediately adjacent N-terminus side of the inserted or substituted residue comprising a nitrogen atom and sulfur atom available for complexation to a metal ion is substituted with Gly, Ala, Ser, Aib, 1-amino, 1-cyclopentane carboxylic acid or ΔAla.

9. The metallopeptide of claim 8 wherein the metal ion is rhenium.

10. The metallopeptide of claim 8 wherein the α-MSH sequence is Ac-Ser-Tyr-Ser-Nle-Glu-His-Phe-Arg-Trp-Gly-Lys-Pro-Val-NH$_2$ (SEQ ID NO:1).

* * * * *

UNITED STATES PATENT AND TRADEMARK OFFICE
CERTIFICATE OF CORRECTION

PATENT NO. : 7,385,025 B2
APPLICATION NO. : 11/188552
DATED : June 10, 2008
INVENTOR(S) : Sharma et al.

It is certified that error appears in the above-identified patent and that said Letters Patent is hereby corrected as shown below:

In Claim 6, Line 6 (corresponding to Column 73, line 5), delete the word "a" after the word "wherein" and before the words "an amino acid".

In Claim 8, Line 6 (corresponding to Column 74, line 5), delete the word "a" after the word "wherein" and before the words "an amino acid".

Signed and Sealed this

Eleventh Day of November, 2008

JON W. DUDAS
*Director of the United States Patent and Trademark Office*